(12) United States Patent
Lee et al.

(10) Patent No.: US 7,217,861 B2
(45) Date of Patent: May 15, 2007

(54) ROOT-SPECIFIC EXPANSIN GENE REGULATING ROOT GROWTH AND OBSTACLE-TOUCHING STRESS RESISTANCE IN THE PLANT

(75) Inventors: Jong Seob Lee, Seoul (KR); Dong-Keun Lee, Seoul (KR); Ji Hoon Ahn, Seoul (KR); Sang-Kee Song, Seoul (KR); Yang Do Choi, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 221 days.

(21) Appl. No.: 10/660,499

(22) Filed: Sep. 12, 2003

(65) Prior Publication Data

US 2005/0246795 A1  Nov. 3, 2005

(30) Foreign Application Priority Data

Mar. 27, 2003 (KR) ...................... 10-2003-0019069

(51) Int. Cl.
*C12N 15/82* (2006.01)
*C12N 15/29* (2006.01)
*C12N 5/10* (2006.01)
*A01H 5/00* (2006.01)
*A01H 5/10* (2006.01)

(52) U.S. Cl. ...................... 800/289; 800/287; 800/278; 800/290; 536/24.1; 536/23.6; 435/320.1; 435/419

(58) Field of Classification Search ...................... None
See application file for complete search history.

(56) References Cited

U.S. PATENT DOCUMENTS 6,166,293 A * 12/2000 Doerner et al. ............. 800/290
2004/0034888 A1 * 2/2004 Liu et al. .................... 800/289

OTHER PUBLICATIONS

Kris Vissenberg, et al, "In Vivo Colocalization of Xyloglucan Endotransglycosylase Activity and Its Donor Substrate in the Elongation Zone of Arabidopsis Roots," The Plant Cell, vol. 12, Jul. 2000, pp. 1229-1237.
Simon McQueen-Mason, et al, "Disruption of hydrogen bonding between plant cell wall polymers by proteins that induce wall extension," Proc. Natl. Acad. Sci., vol. 91, Jul. 1994, pp. 6574-6576.
Daniel J. Cosgrove, "Relaxation in a High-Stress Environment: The Molecular Bases of Extensible cell Walls and Cell Enlargement," The Plant Cell, vol. 9, Jul. 1997, pp. 1031-1041.
Daniel J. Cosgrove, "Cell Wall Loosening by Expansins," Plant Physiol, vol. 118, 1998, pp.333-339.

(Continued)

*Primary Examiner*—David T. Fox
*Assistant Examiner*—Brent T Page
(74) *Attorney, Agent, or Firm*—Joseph Hyosuk Kim; JHK Law

(57) ABSTRACT

The invention relates to root-specific expansin gene to regulating root growth and obstacle-touching stress resistance in the plant, and more particularly to a root growth regulating gene, GmEXP1, isolated from soybean (Glycine max), an expansin polypeptide encoded by the gene and a method for enhancing root growth of plants by overexpression of the gene in the plants.

13 Claims, 15 Drawing Sheets

```
GmEXP1  MGK-IMLVLGSLIGLCCFTIT--TYA------FSPSGWTNAHATFYGGSD
NtEXP3  MAKCCGILALGFIIGF--FSIFFNANA------FTASGWMRAHATFYGCAD
CsEXP2  MEK-LPFAFAFFLALSNFFFLF-VNA------FTASGWAPAHATFYGESD
AtEXP6  MA-----MLGLVLSVSVLTTILALSEARIPGVYNGGGWETAHATFYGGSD
PsEXP1  MA-----AI-LLLTIASLTSLFAPTTARIPGVYTGGPWTSAHATFYGGSD
        *       .   .                 ..*  *******  .*

GmEXP1  ASGTMGGACGYGNLYATGYGTRTAALSTALFNDGASCGQCYKIICDYKSD
NtEXP3  ASGTMGGACGYGNLYSTGYGTRSAALSTALFNSGGSCGQCYKIICDFYAE
CsEXP2  ASGTMGGACGYGNLYQTGYGTRTAALSTALFNDGASCGQCFKIICDYKTD
AtEXP6  ASGTMGGACGYGNLYSQGYGVNTAALSTALFNNGFSCGACFELKCA--SD
PsEXP1  ASGTMGGACGYGNLYSQGYGVNTAALSTALFNNGLSCGACFELKCD--QD
        ******* ******   ***  ,********* * *** *. . *     .

GmEXP1  SRWCIKGR-SVTVTATNFCPPNFALPNNNGGWCNPPLKHFDMAQPAWEKI
NtEXP3  PRWCKKGV-SVTITATNFCPPNYALPSDNGGWCNPPRQHFDMAQPAWEKI
CsEXP2  PRWCIKGA-SVTITATNFCPPNYALPNNNGGWCNPPLKHFDMAQPAWQKI
AtEXP6  PKWCHSGSPSIFITATNFCPPNFAQPSDNGGWCNPPRPHFDLAMPMFLKI
PsEXP1  PRWCNPGNPSILITATNFCPPNFAEPSDNGGWCNPPRPHFDLAMPMFLKI
        ..**  *  *. .*********.* *,.******* ***.* *  **

GmEXP1  GIYRGGIVPVLFQRVPCKKHGGVRFSVNGRDYFELVLISNVGGAGSIQSV
NtEXP3  GVYRGGIIPVFYQRVPCKKRGGVRFTINGRDYFELVLVSNVGGAGSVRSV
CsEXP2  GIYRGGIIPVLYQRVPCKKRGGVRFTVNGRDYFELVLITNVGGAGDIKSV
AtEXP6  AEYRAGIVPVSFRRVPCRKRGGIRFTINGFRYFNLVLVTNVAGAGNIVRL
PsEXP1  AQYRAGIVPVAYRRVPCRKAGGIRFTINGFRYFNLVLITNVAGAGDIVRV
        . **.**.**  ..****.* **. * .**   *.***..**.***

GmEXP1  FIKGSKTG-WMAMSRNWGSNWQSNAYLNGQSLSFRVTTTDGETRVFQDIV
NtEXP3  QIKGSRT-NWMTMSNNWGANFQSNTYLNGQSLSFRVTTTDGVTKTFLNIV
CsEXP2  SIKGSKSSNWTPMSRNWGANWQSNSYLNGQSLSFKVTTSDGQVQVFNNVV
AtEXP6  GVKGTHTS-WMTMSRNWGQNWQSNSVLVGQSLSFRVTSSDRRSSTSWNIA
PsEXP1  SVKGTNTA-WMTMSRNWGQNWQSNAVFVGQALSFRVTGSDRRTSTSWNVA
        *.. . *   ** *** * ***. . **.***.**  .*        ..

GmEXP1  PVSWTFGQTFSSPVQF-
NtEXP3  PANWRFGQTFSSPTQFS
CsEXP2  PSSWRFGQTFASKVQFS
AtEXP6  PANWKFGQTFMGKNFRV
PsEXP1  PPHWQFGQTFTGKNFRV
        *   *  *****  .
```

OTHER PUBLICATIONS

Yi Li, et al, "Plant Expansins Are a Complex Multigene Family with an Ancient Evolutionary Origin," Plant Physiology, vol. 128, Mar. 2002, pp. 854-864.

Bruce M. Link, et al, "Acid-Growth Response and α-Expansins in Suspension Cultures of Bright Yellow 2 Tobacco," Plant Physiol, vol. 118, 1998, pp.907-916.

Hyung-Taeg Cho, et al, "Tissue localization of expansins in deepwater rice," The Plant Journal, vol. 15, No. 6, 1998, pp. 805-812.

Yajun Wu, et al, "Growth Maintenance of the Maize Primary Root at Low Water Potentials Involves Increases in Cell-Wall Extension Properties, Expansin Activity, and Wall Susceptibility to Expansins," Plant Physiol., vol. 111, 1996, pp. 765-772.

Jocelyn K. C. Rose, et al, "Expression of a divergent expansin gene is fruit-specific and ripening-regulated," Proc. Natl. Acad. Sci, vol. 94, May 1997, pp. 5955-5960.

Didier Reinhardt, et al, "Localized Upregulation of a New Expansin Gene Predicts the Site of Leaf Formation in the Tomato Meristern," The Plant Cell. vol. 10, Sep. 1998, pp. 1427-1437.

Kiyotaka Okada, et al, "Reversible Root Tip Rotation in *Arabidopsis* Seedlings Induced by Obstacle-Touching Stimulus," Science, vol. 250, Oct. 12, 1990, pp. 274-276.

\* cited by examiner

FIG. 1

```
GmEXP1   MGK-IMLVLGSLIGLCCFTIT--TYA------FSPSGWTNAHATFYGGSD
NtEXP3   MAKCGILALGFIIGF--FSIFFNANA------FTASGWMRAHATFYGGAD
CsEXP2   MEK-LPFAFAFFLALSNFFFLF-VNA------FTASGWAPAHATFYGESD
AtEXP6   MA-----MLGLVLSVSVLTTILALSEARIPGVYNGGGWETAHATFYGGSD
PsEXP1   MA-----AI-LLLTIASLTSLFAPTTARIPGVYTGGPWTSAHATFYGGSD
         *        .  .   .              . . * ******* .*

GmEXP1   ASGTMGGACGYGNLYATGYGTRTAALSTALFNDGASCGQCYKIICDYKSD
NtEXP3   ASGTMGGACGYGNLYSTGYGTRSAALSTALFNSGGSCGQCYKIICDFYAE
CsEXP2   ASGTMGGACGYGNLYQTGYGTRTAALSTALFNDGASCGQCFKIICDYKTD
AtEXP6   ASGTMGGACGYGNLYSQGYGVNTAALSTALFNNGFSCGACFELKCA--SD
PsEXP1   ASGTMGGACGYGNLYSQGYGVNTAALSTALFNNGLSCGACFELKCD--QD
         ******* *******  *** .********* * *** *. . *    .

GmEXP1   SRWCIKGR-SVTVTATNFCPPNFALPNNNGGWCNPPLKHFDMAQPAWEKI
NtEXP3   PRWCKKGV-SVTITATNFCPPNYALPSDNGGWCNPPRQHFDMAQPAWEKI
CsEXP2   PRWCIKGA-SVTITATNFCPPNYALPNNNGGWCNPPLKHFDMAQPAWQKI
AtEXP6   PKWCHSGSPSIFITATNFCPPNFAQPSDNGGWCNPPRPHFDLAMPMFLKI
PsEXP1   PRWCNPGNPSILITATNFCPPNFAEPSDNGGWCNPPRPHFDLAMPMFLKI
         ..**  *   *. .*********.* *..******** ***.* *   **

GmEXP1   GIYRGGIVPVLFQRVPCKKHGGVRFSVNGRDYFELVLISNVGGAGSIQSV
NtEXP3   GVYRGGIIPVFYQRVPCKKRGGVRFTINGRDYFELVLVSNVGGAGSVRSV
CsEXP2   GIYRGGIIPVLYQRVPCKKRGGVRFTVNGRDYFELVLITNVGGAGDIKSV
AtEXP6   AEYRAGIVPVSFRRVPCRKRGGIRFTINGFRYFNLVLVTNVAGAGNIVRL
PsEXP1   AQYRAGIVPVAYRRVPCRKAGGIRFTINGFRYFNLVLITNVAGAGDIVRV
         . **.**.**  ..****.* **. * .**   *.***..**.***

GmEXP1   FIKGSKTG-WMAMSRNWGSNWQSNAYLNGQSLSFRVTTTDGETRVFQDIV
NtEXP3   QIKGSRT-NWMTMSNNWGANFQSNTYLNGQSLSFRVTTTDGVTKTFLNIV
CsEXP2   SIKGSKSSNWTPMSRNWGANWQSNSYLNGQSLSFKVTTSDGQVQVFNNVV
AtEXP6   GVKGTHTS-WMTMSRNWGQNWQSNSVLVGQSLSFRVTSSDRRSSTSWNIA
PsEXP1   SVKGTNTA-WMTMSRNWGQNWQSNAVFVGQALSFRVTGSDRRTSTSWNVA
         *. .  *  ** ***  ***. . **.***.** .*         ..

GmEXP1   PVSWTFGQTFSSPVQF-
NtEXP3   PANWRFGQTFSSPTQFS
CsEXP2   PSSWRFGQTFASKVQFS
AtEXP6   PANWKFGQTFMGKNFRV
PsEXP1   PPHWQFGQTFTGKNFRV
         *  *  *****   .
```

FIG. 4
A  B  C  D
 GmEXP1
 25S rRNA

FIG. 7
 GmEXP1
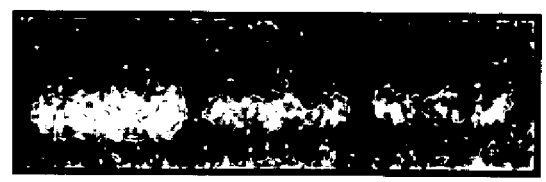 25S rRNA

FIG. 8
A
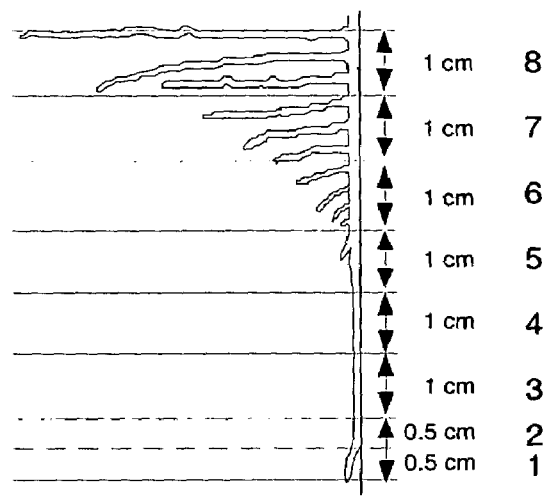
B
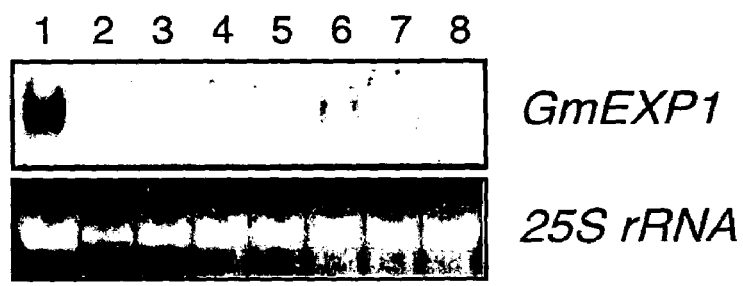
GmEXP1
25S rRNA
C
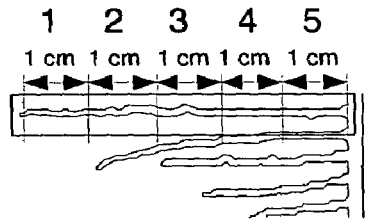
D
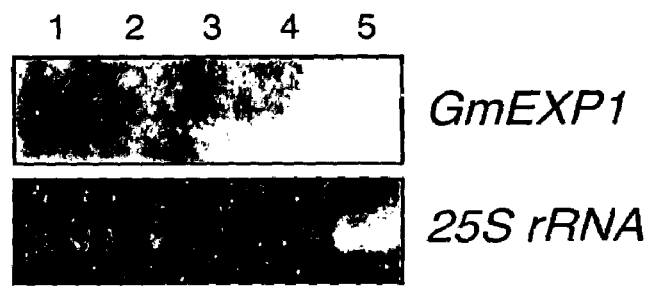
GmEXP1
25S rRNA

SEQUENCE LISTING

<160> NUMBER OF SEQ ID NOS: 9

<210> SEQ ID NO 1
<211> LENGTH: 1089
<212> TYPE: DNA
<213> ORGANISM: Glycine max
<220> FEATURE:
<221> NAME/KEY: CDS
<222> LOCATION: (52)..(816)
<223> OTHER INFORMATION: Glycine max expansin (GmEXP1)

<400> SEQUENCE: 1

```
gcacgagctt caacctctca tcattaggca ttcagcaagc aagaaaaaaa a atg ggc      57
                                                          Met Gly
                                                          1 aaa atc atg ctt gtt ttg ggt agc ctc att gga tta tgc tgt ttc aca     105
Lys Ile Met Leu Val Leu Gly Ser Leu Ile Gly Leu Cys Cys Phe Thr
        5                  10                  15 atc act acc tat gcc ttc tca cct tct gga tgg acc aac gcc cat gcc     153
Ile Thr Thr Tyr Ala Phe Ser Pro Ser Gly Trp Thr Asn Ala His Ala
 20                  25                  30 act ttt tat ggg ggt agt gat gct tca gga act atg ggg gga gct tgt     201
Thr Phe Tyr Gly Gly Ser Asp Ala Ser Gly Thr Met Gly Gly Ala Cys
35                  40                  45                  50 ggg tat ggg aat ctg tat gca act ggg tat gga act aga act gca gct     249
Gly Tyr Gly Asn Leu Tyr Ala Thr Gly Tyr Gly Thr Arg Thr Ala Ala
                55                  60                  65 tta agc act gcc tta ttt aat gat gga gct tcc tgt ggt cag tgc tac     297
Leu Ser Thr Ala Leu Phe Asn Asp Gly Ala Ser Cys Gly Gln Cys Tyr
            70                  75                  80 aaa att ata tgt gat tac aaa tca gac tct aga tgg tgc atc aaa gga     345
Lys Ile Ile Cys Asp Tyr Lys Ser Asp Ser Arg Trp Cys Ile Lys Gly
        85                  90                  95 aga tct gta acc gta act gcc aca aac ttt tgc cct ccc aat ttc gcc     393
Arg Ser Val Thr Val Thr Ala Thr Asn Phe Cys Pro Pro Asn Phe Ala
100                 105                 110 ctt cct aac aac aat gga ggc tgg tgc aac cca cca ctc aag cat ttt     441
Leu Pro Asn Asn Asn Gly Gly Trp Cys Asn Pro Pro Leu Lys His Phe
115                 120                 125                 130 gat atg gcc caa ccc gct tgg gaa aag att ggt att tac aga gga ggg     489
Asp Met Ala Gln Pro Ala Trp Glu Lys Ile Gly Ile Tyr Arg Gly Gly
                135                 140                 145 atc gtc ccc gtg cta ttt caa agg gtt cca tgc aaa aag cat gga ggg     537
Ile Val Pro Val Leu Phe Gln Arg Val Pro Cys Lys Lys His Gly Gly
            150                 155                 160 gtt agg ttc agt gtg aat ggg agg gac tac ttt gag cta gta ttg atc     585
Val Arg Phe Ser Val Asn Gly Arg Asp Tyr Phe Glu Leu Val Leu Ile
        165                 170                 175 agc aat gtg ggg ggt gct gga tcc atc caa tca gtg ttc att aaa ggc     633
Ser Asn Val Gly Gly Ala Gly Ser Ile Gln Ser Val Phe Ile Lys Gly
180                 185                 190 tca aaa act gga tgg atg gca atg tca aga aat tgg ggt tct aat tgg     681
Ser Lys Thr Gly Trp Met Ala Met Ser Arg Asn Trp Gly Ser Asn Trp
195                 200                 205                 210 caa tcc aat gcg tat ttg aat ggt caa tct ttg tcc ttc agg gtc acc     729
Gln Ser Asn Ala Tyr Leu Asn Gly Gln Ser Leu Ser Phe Arg Val Thr
                215                 220                 225 acc act gat gga gag acc aga gtt ttc caa gat att gtt cca gta agt     777
Thr Thr Asp Gly Glu Thr Arg Val Phe Gln Asp Ile Val Pro Val Ser
            230                 235                 240 tgg aca ttc ggc caa act ttc tct agc cca gtt cag ttc taagctgatt     826
Trp Thr Phe Gly Gln Thr Phe Ser Ser Pro Val Gln Phe
        245                 250                 255 acagataaac caaccaacgg ctgaggcgtg cttttttatt ttattactgg agctgcccgc   886 caccctttctt ctggttttga ttattcccat caactccaag ccctctatca aggcataaat  946
```

```
tcttatcaat aatacaatca atcaccatca tatcatcata agcttgtata tcaaataaac    1006
atctttcaag tttaaattaa tttatactat aaattgttgt aatatcatta tagttgaagt    1066
tcaaaaaaaa aaaaaaaaaa aaa                                            1089
```

```
<210> SEQ ID NO 2
<211> LENGTH: 255
<212> TYPE: PRT
<213> ORGANISM: Glycine max

<400> SEQUENCE: 2

Met Gly Lys Ile Met Leu Val Leu Gly Ser Leu Ile Gly Leu Cys Cys
1               5                   10                  15

Phe Thr Ile Thr Thr Tyr Ala Phe Ser Pro Ser Gly Trp Thr Asn Ala
            20                  25                  30

His Ala Thr Phe Tyr Gly Gly Ser Asp Ala Ser Gly Thr Met Gly Gly
        35                  40                  45

Ala Cys Gly Tyr Gly Asn Leu Tyr Ala Thr Gly Tyr Gly Thr Arg Thr
    50                  55                  60

Ala Ala Leu Ser Thr Ala Leu Phe Asn Asp Gly Ala Ser Cys Gly Gln
65                  70                  75                  80

Cys Tyr Lys Ile Ile Cys Asp Tyr Lys Ser Asp Ser Arg Trp Cys Ile
                85                  90                  95

Lys Gly Arg Ser Val Thr Val Thr Ala Thr Asn Phe Cys Pro Pro Asn
            100                 105                 110

Phe Ala Leu Pro Asn Asn Asn Gly Gly Trp Cys Asn Pro Pro Leu Lys
        115                 120                 125

His Phe Asp Met Ala Gln Pro Ala Trp Glu Lys Ile Gly Ile Tyr Arg
    130                 135                 140

Gly Gly Ile Val Pro Val Leu Phe Gln Arg Val Pro Cys Lys Lys His
145                 150                 155                 160

Gly Gly Val Arg Phe Ser Val Asn Gly Arg Asp Tyr Phe Glu Leu Val
                165                 170                 175

Leu Ile Ser Asn Val Gly Gly Ala Gly Ser Ile Gln Ser Val Phe Ile
            180                 185                 190

Lys Gly Ser Lys Thr Gly Trp Met Ala Met Ser Arg Asn Trp Gly Ser
        195                 200                 205

Asn Trp Gln Ser Asn Ala Tyr Leu Asn Gly Gln Ser Leu Ser Phe Arg
    210                 215                 220

Val Thr Thr Thr Asp Gly Glu Thr Arg Val Phe Gln Asp Ile Val Pro
225                 230                 235                 240

Val Ser Trp Thr Phe Gly Gln Thr Phe Ser Ser Pro Val Gln Phe
                245                 250                 255

<210> SEQ ID NO 3
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(2)
<223> OTHER INFORMATION: n is a, c, g, or t.
<220> FEATURE:
<221> NAME/KEY: misc_feature
<222> LOCATION: (14)..(14)
<223> OTHER INFORMATION: n is a, c, g, or t.
<220> FEATURE:
<221> NAME/KEY: misc_feature
```

-continued

```
<222> LOCATION: (17)..(17)
<223> OTHER INFORMATION: n is a, c, g, or t.
<220> FEATURE:
<221> NAME/KEY: misc_feature
<222> LOCATION: (20)..(20)
<223> OTHER INFORMATION: n is a, c, g, or t.
<220> FEATURE:
<221> NAME/KEY: misc_feature
<222> LOCATION: (23)..(23)
<223> OTHER INFORMATION: n is a, c, g, or t.
<220> FEATURE:
<221> NAME/KEY: misc_feature
<222> LOCATION: (42)..(42)
<223> OTHER INFORMATION: n is a, c, g, or t.

<400> SEQUENCE: 3
nnggatccga ygcntcnggn acnatgggyg gygctgygyt angg                44

<210> SEQ ID NO 4
<211> LENGTH: 37
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(2)
<223> OTHER INFORMATION: n is a, c, g, or t.
<220> FEATURE:
<221> NAME/KEY: misc_feature
<222> LOCATION: (23)..(24)
<223> OTHER INFORMATION: n is a, c, g, or t.
<220> FEATURE:
<221> NAME/KEY: misc_feature
<222> LOCATION: (26)..(26)
<223> OTHER INFORMATION: n is a, c, g, or t.
<220> FEATURE:
<221> NAME/KEY: misc_feature
<222> LOCATION: (35)..(35)
<223> OTHER INFORMATION: n is a, c, g, or t.

<400> SEQUENCE: 4
nnggatcctt kswytgccar ttnnsncccc arttnck                        37

<210> SEQ ID NO 5
<211> LENGTH: 519
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (6)..(6)
<223> OTHER INFORMATION: n is a, c, g, or t.
<220> FEATURE:
<221> NAME/KEY: misc_feature
<222> LOCATION: (9)..(9)
<223> OTHER INFORMATION: n is a, c, g, or t.
<220> FEATURE:
<221> NAME/KEY: misc_feature
<222> LOCATION: (12)..(12)
<223> OTHER INFORMATION: n is a, c, g, or t.
<220> FEATURE:
<221> NAME/KEY: misc_feature
<222> LOCATION: (15)..(15)
<223> OTHER INFORMATION: n is a, c, g, or t.
<220> FEATURE:
<221> NAME/KEY: misc_feature
<222> LOCATION: (21)..(21)
<223> OTHER INFORMATION: n is a, c, g, or t.
<220> FEATURE:
<221> NAME/KEY: misc_feature
<222> LOCATION: (24)..(24)
<223> OTHER INFORMATION: n is a, c, g, or t.
<220> FEATURE:
```

-continued

```
<221> NAME/KEY: misc_feature
<222> LOCATION: (27)..(27)
<223> OTHER INFORMATION: n is a, c, g, or t.
<220> FEATURE:
<221> NAME/KEY: misc_feature
<222> LOCATION: (33)..(33)
<223> OTHER INFORMATION: n is a, c, g, or t.
<220> FEATURE:
<221> NAME/KEY: misc_feature
<222> LOCATION: (39)..(39)
<223> OTHER INFORMATION: n is a, c, g, or t.
<220> FEATURE:
<221> NAME/KEY: misc_feature
<222> LOCATION: (45)..(45)
<223> OTHER INFORMATION: n is a, c, g, or t.
<220> FEATURE:
<221> NAME/KEY: misc_feature
<222> LOCATION: (51)..(51)
<223> OTHER INFORMATION: n is a, c, g, or t.
<220> FEATURE:
<221> NAME/KEY: misc_feature
<222> LOCATION: (54)..(54)
<223> OTHER INFORMATION: n is a, c, g, or t.
<220> FEATURE:
<221> NAME/KEY: misc_feature
<222> LOCATION: (57)..(57)
<223> OTHER INFORMATION: n is a, c, g, or t.
<220> FEATURE:
<221> NAME/KEY: misc_feature
<222> LOCATION: (63)..(63)
<223> OTHER INFORMATION: n is a, c, g, or t.
<220> FEATURE:
<221> NAME/KEY: misc_feature
<222> LOCATION: (66)..(66)
<223> OTHER INFORMATION: n is a, c, g, or t.
<220> FEATURE:
<221> NAME/KEY: misc_feature
<222> LOCATION: (69)..(69)
<223> OTHER INFORMATION: n is a, c, g, or t.
<220> FEATURE:
<221> NAME/KEY: misc_feature
<222> LOCATION: (71)..(71)
<223> OTHER INFORMATION: n is a, c, g, or t.
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t.
<220> FEATURE:
<221> NAME/KEY: misc_feature
<222> LOCATION: (78)..(78)
<223> OTHER INFORMATION: n is a, c, g, or t.
<220> FEATURE:
<221> NAME/KEY: misc_feature
<222> LOCATION: (81)..(81)
<223> OTHER INFORMATION: n is a, c, g, or t.
<220> FEATURE:
<221> NAME/KEY: misc_feature
<222> LOCATION: (84)..(84)
<223> OTHER INFORMATION: n is a, c, g, or t.
<220> FEATURE:
<221> NAME/KEY: misc_feature
<222> LOCATION: (87)..(87)
<223> OTHER INFORMATION: n is a, c, g, or t.
<220> FEATURE:
<221> NAME/KEY: misc_feature
<222> LOCATION: (90)..(90)
<223> OTHER INFORMATION: n is a, c, g, or t.
<220> FEATURE:
<221> NAME/KEY: misc_feature
<222> LOCATION: (93)..(93)
<223> OTHER INFORMATION: n is a, c, g, or t.
<220> FEATURE:
<221> NAME/KEY: misc_feature
<222> LOCATION: (105)..(105)
<223> OTHER INFORMATION: n is a, c, g, or t.
```

-continued

```
<220> FEATURE:
<221> NAME/KEY: misc_feature
<222> LOCATION: (108)..(108)
<223> OTHER INFORMATION: n is a, c, g, or t.
<220> FEATURE:
<221> NAME/KEY: misc_feature
<222> LOCATION: (111)..(111)
<223> OTHER INFORMATION: n is a, c, g, or t.
<220> FEATURE:
<221> NAME/KEY: misc_feature
<222> LOCATION: (117)..(117)
<223> OTHER INFORMATION: n is a, c, g, or t.
<220> FEATURE:
<221> NAME/KEY: misc_feature
<222> LOCATION: (150)..(150)
<223> OTHER INFORMATION: n is a, c, g, or t.
<220> FEATURE:
<221> NAME/KEY: misc_feature
<222> LOCATION: (156)..(156)
<223> OTHER INFORMATION: n is a, c, g, or t.
<220> FEATURE:
<221> NAME/KEY: misc_feature
<222> LOCATION: (159)..(159)
<223> OTHER INFORMATION: n is a, c, g, or t.
<220> FEATURE:
<221> NAME/KEY: misc_feature
<222> LOCATION: (174)..(174)
<223> OTHER INFORMATION: n is a, c, g, or t.
<220> FEATURE:
<221> NAME/KEY: misc_feature
<222> LOCATION: (177)..(177)
<223> OTHER INFORMATION: n is a, c, g, or t.
<220> FEATURE:
<221> NAME/KEY: misc_feature
<222> LOCATION: (180)..(180)
<223> OTHER INFORMATION: n is a, c, g, or t.
<220> FEATURE:
<221> NAME/KEY: misc_feature
<222> LOCATION: (183)..(183)
<223> OTHER INFORMATION: n is a, c, g, or t.
<220> FEATURE:
<221> NAME/KEY: misc_feature
<222> LOCATION: (186)..(186)
<223> OTHER INFORMATION: n is a, c, g, or t.
<220> FEATURE:
<221> NAME/KEY: misc_feature
<222> LOCATION: (189)..(189)
<223> OTHER INFORMATION: n is a, c, g, or t.
<220> FEATURE:
<221> NAME/KEY: misc_feature
<222> LOCATION: (192)..(192)
<223> OTHER INFORMATION: n is a, c, g, or t.
<220> FEATURE:
<221> NAME/KEY: misc_feature
<222> LOCATION: (195)..(195)
<223> OTHER INFORMATION: n is a, c, g, or t.
<220> FEATURE:
<221> NAME/KEY: misc_feature
<222> LOCATION: (198)..(198)
<223> OTHER INFORMATION: n is a, c, g, or t.
<220> FEATURE:
<221> NAME/KEY: misc_feature
<222> LOCATION: (210)..(210)
<223> OTHER INFORMATION: n is a, c, g, or t.
<220> FEATURE:
<221> NAME/KEY: misc_feature
<222> LOCATION: (213)..(213)
<223> OTHER INFORMATION: n is a, c, g, or t.
<220> FEATURE:
<221> NAME/KEY: misc_feature
<222> LOCATION: (222)..(222)
<223> OTHER INFORMATION: n is a, c, g, or t.
<220> FEATURE:
<221> NAME/KEY: misc_feature
<222> LOCATION: (225)..(225)
<223> OTHER INFORMATION: n is a, c, g, or t.
<220> FEATURE:
<221> NAME/KEY: misc_feature
<222> LOCATION: (228)..(228)
```

-continued

```
<223> OTHER INFORMATION: n is a, c, g, or t.
<220> FEATURE:
<221> NAME/KEY: misc_feature
<222> LOCATION: (240)..(240)
<223> OTHER INFORMATION: n is a, c, g, or t.
<220> FEATURE:
<221> NAME/KEY: misc_feature
<222> LOCATION: (243)..(243)
<223> OTHER INFORMATION: n is a, c, g, or t.
<220> FEATURE:
<221> NAME/KEY: misc_feature
<222> LOCATION: (255)..(255)
<223> OTHER INFORMATION: n is a, c, g, or t.
<220> FEATURE:
<221> NAME/KEY: misc_feature
<222> LOCATION: (258)..(258)
<223> OTHER INFORMATION: n is a, c, g, or t.
<220> FEATURE:
<221> NAME/KEY: misc_feature
<222> LOCATION: (261)..(261)
<223> OTHER INFORMATION: n is a, c, g, or t.
<220> FEATURE:
<221> NAME/KEY: misc_feature
<222> LOCATION: (279)..(279)
<223> OTHER INFORMATION: n is a, c, g, or t.
<220> FEATURE:
<221> NAME/KEY: misc_feature
<222> LOCATION: (285)..(285)
<223> OTHER INFORMATION: n is a, c, g, or t.
<220> FEATURE:
<221> NAME/KEY: misc_feature
<222> LOCATION: (288)..(288)
<223> OTHER INFORMATION: n is a, c, g, or t.
<220> FEATURE:
<221> NAME/KEY: misc_feature
<222> LOCATION: (303)..(303)
<223> OTHER INFORMATION: n is a, c, g, or t.
<220> FEATURE:
<221> NAME/KEY: misc_feature
<222> LOCATION: (312)..(312)
<223> OTHER INFORMATION: n is a, c, g, or t.
<220> FEATURE:
<221> NAME/KEY: misc_feature
<222> LOCATION: (315)..(315)
<223> OTHER INFORMATION: n is a, c, g, or t.
<220> FEATURE:
<221> NAME/KEY: misc_feature
<222> LOCATION: (318)..(318)
<223> OTHER INFORMATION: n is a, c, g, or t.
<220> FEATURE:
<221> NAME/KEY: misc_feature
<222> LOCATION: (324)..(324)
<223> OTHER INFORMATION: n is a, c, g, or t.
<220> FEATURE:
<221> NAME/KEY: misc_feature
<222> LOCATION: (327)..(327)
<223> OTHER INFORMATION: n is a, c, g, or t.
<220> FEATURE:
<221> NAME/KEY: misc_feature
<222> LOCATION: (330)..(330)
<223> OTHER INFORMATION: n is a, c, g, or t.
<220> FEATURE:
<221> NAME/KEY: misc_feature
<222> LOCATION: (333)..(333)
<223> OTHER INFORMATION: n is a, c, g, or t.
<220> FEATURE:
<221> NAME/KEY: misc_feature
<222> LOCATION: (342)..(342)
<223> OTHER INFORMATION: n is a, c, g, or t.
<220> FEATURE:
<221> NAME/KEY: misc_feature
<222> LOCATION: (345)..(345)
<223> OTHER INFORMATION: n is a, c, g, or t.
<220> FEATURE:
<221> NAME/KEY: misc_feature
<222> LOCATION: (348)..(348)
<223> OTHER INFORMATION: n is a, c, g, or t.
<220> FEATURE:
<221> NAME/KEY: misc_feature
```

```
<222> LOCATION: (363)..(363)
<223> OTHER INFORMATION: n is a, c, g, or t.
<220> FEATURE:
<221> NAME/KEY: misc_feature
<222> LOCATION: (366)..(366)
<223> OTHER INFORMATION: n is a, c, g, or t.
<220> FEATURE:
<221> NAME/KEY: misc_feature
<222> LOCATION: (369)..(369)
<223> OTHER INFORMATION: n is a, c, g, or t.
<220> FEATURE:
<221> NAME/KEY: misc_feature
<222> LOCATION: (372)..(372)
<223> OTHER INFORMATION: n is a, c, g, or t.
<220> FEATURE:
<221> NAME/KEY: misc_feature
<222> LOCATION: (378)..(378)
<223> OTHER INFORMATION: n is a, c, g, or t.
<220> FEATURE:
<221> NAME/KEY: misc_feature
<222> LOCATION: (381)..(381)
<223> OTHER INFORMATION: n is a, c, g, or t.
<220> FEATURE:
<221> NAME/KEY: misc_feature
<222> LOCATION: (387)..(387)
<223> OTHER INFORMATION: n is a, c, g, or t.
<220> FEATURE:
<221> NAME/KEY: misc_feature
<222> LOCATION: (390)..(390)
<223> OTHER INFORMATION: n is a, c, g, or t.
<220> FEATURE:
<221> NAME/KEY: misc_feature
<222> LOCATION: (405)..(405)
<223> OTHER INFORMATION: n is a, c, g, or t.
<220> FEATURE:
<221> NAME/KEY: misc_feature
<222> LOCATION: (408)..(408)
<223> OTHER INFORMATION: n is a, c, g, or t.
<220> FEATURE:
<221> NAME/KEY: misc_feature
<222> LOCATION: (411)..(411)
<223> OTHER INFORMATION: n is a, c, g, or t.
<220> FEATURE:
<221> NAME/KEY: misc_feature
<222> LOCATION: (417)..(417)
<223> OTHER INFORMATION: n is a, c, g, or t.
<220> FEATURE:
<221> NAME/KEY: misc_feature
<222> LOCATION: (423)..(423)
<223> OTHER INFORMATION: n is a, c, g, or t.
<220> FEATURE:
<221> NAME/KEY: misc_feature
<222> LOCATION: (426)..(426)
<223> OTHER INFORMATION: n is a, c, g, or t.
<220> FEATURE:
<221> NAME/KEY: misc_feature
<222> LOCATION: (429)..(429)
<223> OTHER INFORMATION: n is a, c, g, or t.
<220> FEATURE:
<221> NAME/KEY: misc_feature
<222> LOCATION: (432)..(432)
<223> OTHER INFORMATION: n is a, c, g, or t.
<220> FEATURE:
<221> NAME/KEY: misc_feature
<222> LOCATION: (435)..(435)
<223> OTHER INFORMATION: n is a, c, g, or t.
<220> FEATURE:
<221> NAME/KEY: misc_feature
<222> LOCATION: (438)..(438)
<223> OTHER INFORMATION: n is a, c, g, or t.
<220> FEATURE:
<221> NAME/KEY: misc_feature
<222> LOCATION: (447)..(447)
<223> OTHER INFORMATION: n is a, c, g, or t.
<220> FEATURE:
<221> NAME/KEY: misc_feature
<222> LOCATION: (450)..(450)
<223> OTHER INFORMATION: n is a, c, g, or t.
<220> FEATURE:
```

-continued

<221> NAME/KEY: misc_feature
<222> LOCATION: (462)..(462)
<223> OTHER INFORMATION: n is a, c, g, or t.
<220> FEATURE:
<221> NAME/KEY: misc_feature
<222> LOCATION: (465)..(465)
<223> OTHER INFORMATION: n is a, c, g, or t.
<220> FEATURE:
<221> NAME/KEY: misc_feature
<222> LOCATION: (471)..(471)
<223> OTHER INFORMATION: n is a, c, g, or t.
<220> FEATURE:
<221> NAME/KEY: misc_feature
<222> LOCATION: (474)..(474)
<223> OTHER INFORMATION: n is a, c, g, or t.
<220> FEATURE:
<221> NAME/KEY: misc_feature
<222> LOCATION: (483)..(483)
<223> OTHER INFORMATION: n is a, c, g, or t.
<220> FEATURE:
<221> NAME/KEY: misc_feature
<222> LOCATION: (489)..(489)
<223> OTHER INFORMATION: n is a, c, g, or t.
<220> FEATURE:
<221> NAME/KEY: misc_feature
<222> LOCATION: (492)..(492)
<223> OTHER INFORMATION: n is a, c, g, or t.
<220> FEATURE:
<221> NAME/KEY: misc_feature
<222> LOCATION: (501)..(501)
<223> OTHER INFORMATION: n is a, c, g, or t.
<220> FEATURE:
<221> NAME/KEY: misc_feature
<222> LOCATION: (504)..(504)
<223> OTHER INFORMATION: n is a, c, g, or t.
<220> FEATURE:
<221> NAME/KEY: misc_feature
<222> LOCATION: (516)..(516)
<223> OTHER INFORMATION: n is a, c, g, or t.

<400> SEQUENCE: 5
gaygcnwsng gnacnatggg nggngcntgy ggntayggna ayytntaygc nacnggntay 60
ggnacnmgna cngcngcnyt nwsnacngcn ytnttyaayg ayggngcnws ntgyggncar 120
tgytayaara thathtgyga ytayaarwsn gaywsnmgnt ggtgyathaa rggnmgnwsn 180
gtnacngtna cngcnacnaa yttytgyccn ccnaayttyg cnytnccnaa yaayaayggn 240
ggntggtgya ayccnccnyt naarcaytty gayatggcnc arccngcntg ggaraarath 300
ggnathtaym gnggnggnat hgtnccngtn ytnttycarm gngtnccntg yaaraarcay 360
ggnggngtnm gnttywsngt naayggnmgn gaytayttyg arytngtnyt nathwsnaay 420
gtnggnggng cnggnwsnat hcarwsngtn ttyathaarg gnwsnaarac nggntggatg 480
gcnatgwsnm gnaaytgggg nwsnaaytgg carwsnaay 519

<210> SEQ ID NO 6
<211> LENGTH: 269
<212> TYPE: RNA
<213> ORGANISM: Artificial Sequence
<220> FEATURE:
<223> OTHER INFORMATION: RNA Probe (antisense)

<400> SEQUENCE: 6
aauaaaauaa aaaagcacgc cucagccguu gguugguuua ucuguaauca gcuuagaacu 60
gaacugggcu agagaaaguu uggccgaaug uccaacuuac uggaacaaua ucuuggaaaa 120
cucuggucuc uccaucagug guggugaccc ugaaggacaa agauugacca uucaaauacg 180
cauuggauug ccaauuagaa ccccaauuuc uugacauugc cauccaucca guuuuugagc 240
cuuuaaugaa cacugauugg auggaucca 269

```
<210> SEQ ID NO 7
<211> LENGTH: 389
<212> TYPE: RNA
<213> ORGANISM: Artificial Sequence
<220> FEATURE:
<223> OTHER INFORMATION: RNA probe (sense)

<400> SEQUENCE: 7
uggauccauc caaucagugu ucauuaaagg cucaaaaacu ggauggaugg caaugucaag      60 aaauggggu ucuaauuggc aauccaaugc guauuugaau ggucaaucuu uguccuucag      120
ggucaccacc acugauggag agaccagagu uuccaagau auuguuccag uaaguuggac      180
auucggccaa acuuucucua gcccaguuca guucuaagcu gauuacagau aaaccaacca      240
acggcugagg cgugcuuuuu uauuuuauua cuggagcugc ccgccacccu ucuucugguu      300
uugauuauuc ccaucaacuc caagcccucu aucaaggcau aaauucuuau caauaauaca      360
aucaaucacc aucauaucau cauaagcuu                                        389

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
accaagcttc aacctctcat cattaggc                                         28

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
accaagcttg gagttgatgg gaataatca                                        29
```

ROOT-SPECIFIC EXPANSIN GENE REGULATING ROOT GROWTH AND OBSTACLE-TOUCHING STRESS RESISTANCE IN THE PLANT

This application claims the priority of Korea Patent Application No. 2003-19069, filed Mar. 27, 2003.

FIELD OF THE INVENTION

The present invention relates to root-specific expansin gene regulating root growth and obstacle-touching stress resistance in plants.

BACKGROUND OF THE INVENTION

A root is a plant organ that has adapted to acquire water and nutrients from the environment (Schiefelbein J. W. et al., *Plant Cell*, 9:1089–1098, 1997). A root consists of epidermis, cortex and vascular tissues in radial rows or concentric circles (Esau K., *Anatomy of Seed Plants*, Ed. 2, 215–245, 1997; Dolan L. et al., *Development*, 119:71–84, 1993; Raven P. H. et al., *Biology of Plants*, 6$^{th}$ Ed. Worth Publishers, New York, 1999). In the longitudinal section, a root can be divided into three different regions; cell division, elongation and maturation region (Dolan L. et al., *Development*, 119: 71–84, 1993; Baluska F. et al., *Plant Physiol.*, 112:3–4, 1996). The region of cell division carries out new cell divisions. The cells derived from the region of cell division expand and elongate mostly in the region of elongation. The elongated cells begin to differentiate in a region of maturation, where root hairs and secondary roots are initiated. The cell elongation and maturation in a root are controlled by the extensibility of cell wall and the turgor pressure inside the cell (Cosgrove D. J., *BioEssays*, 18533–540, 1996).

It is known that the extent of plant cell elongation is confined by cell walls. The cell wall is composed of polysaccharides, proteins, phenolic compounds and other materials (Varner J. E. et al., *Cell*, 56:231–239, 1989). The plant cell wall plays a determinative role in establishing the size and shape of a plant cell. For elongation or maturation, however, a plant cell needs to selectively modify its cell wall. The agents for cell wall modification in the plant cell include various cell wall components, such as expansins, endoglucanases, xyloglucan endotransglycosylases and hydroxyl radicals (Cosgrove D. J., *Annu. Rev. Plant Physiol. Plant Mol. Biol.*, 50:391–417, 1999; Cosgrove D. J., *Plant Physiol. Biochem.*, 38:109–124, 2000a; Cosgrove D. J., *Nature*, 407:321–326, 2000b).

Expansins are generally considered as primary agents for cell wall elongation (Vissenberg K. et al., *Plant Cell*, 12:1229–1237, 2000). Expansins cause wall creep by loosening hydrogen bonds between cellulose microfibrils and matrix polymer (McQeen-Mason S. et al., *Proc. Natl. Acad. Sci. USA*, 91:6574–6578, 1994; Cosgrove D. J., *Plant Cell*, 9:1031–1041, 1997). Since the first cloning of an expansin gene (Shcherban T. Y. et al., *Proc. Natl. Acad. Sci. USA*, 92:9245–9249, 1995), many expansin genes have been identified from a variety of plant species. And they are known to form a multigene family (Cosgrove D. J., *Plant Physiol.*, 118:333–339, 1998). The expansin genes are classified into three subfamilies, α-, β- and γ-expansin subfamilies, based on their phylogenetic relationship (Li Y. et al., *Plant Physiol.*, 128:854–864, 2002). The (α-expansins compose a major portion of the expansins, including the ones from tomato (*Lycopersicon esculentum*) (Keller E. et al., *Plant J.*, 8:795–802, 1995), rice (*Oryza sativa*) (Cho H-T. et al., *Plant Physiol.*, 113:1137–1143, 1997a), oat (*Avena sativa*) (Li Z-C et al., *Planta*, 191:349–356, 1993) and *Arabidopsis*(*Arabidopsis thaliana*) (Cosgrove D. J., *Plant Physiol.*, 118: 333–339, 1998; Li Y. et al., *Plant Physiol.*, 128:854–864, 2002). The α-expansin subfamily can be further divided into A, B, C and D groups (Link B. M. et al., *Plant Physiol*, 118:907–916, 1998).

Expression patterns of the α-expansin genes have been extensively studied in deepwater rice and tomato. It was reported that the transcript of an expansin gene in deepwater rice, OsEXP4, increases in abundance before onset of cell wall extensibility and faster growth, supporting the role of expansins in cell elongation (Cho H-T et al., *Plant J*, 15:805–812, 1998). Also, in tomato, expression of the LeEXP18 gene was localized in a group of cells in the shoot apical meristem where incipient leaf primordium initiation takes place (Reinhardt D. et al., *Plant Cell*, 10:1427–1437, 1998). International Patent Publication No. WO02086066 discloses a novel β-expansin polypeptide for modifying the structure of cell walls in a plant and a nucleotide sequence encoding the same. U.S. Pat. No. 5,929,303 discloses a fruit-specific and ripening regulation expansin gene.

Studies of a variety of expansin genes and their tissue-specific expression patterns show that different expansin genes may play different roles in various cell types during organ development in plants (Rose et al., *Proc. Natl. Acad. Sci*, USA, 94:5955–5950, 1997). Therefore, it is still necessary to study new expansin genes and their functions.

SUMMARY OF THE INVENTION

The present invention is based on the isolation and characterization of a new expansin gene that regulates root growth and obstacle-touching stress resistance in plants.

The present invention provides an isolated polynucleotide encoding a root growth regulating polypeptide, wherein the polypeptide comprising an amino acid sequence with at least 90% sequence homology to SEQ ID NO: 2 or an amino acid sequence set forth in SEQ ID NO: 2.

The invention also provides a recombinant vector comprising the polynucleotide.

The invention also provides a cell comprising the polynucleotide

The invention also provides a plant comprising the polynucleotide.

The invention also provides a plant tissue or seed derived from the plant.

The invention also provides a method for enhancing root growth of a plant, comprising the step of introducing the above polynucleotide into the plant cell, wherein the polynucleotide being operably linked to the expression control sequence The invention also provides enhancing resistance in a plant to obstacle-touching stress, comprising the step of introducing the above polynucleotide into the plant cell, wherein the polynucleotide being operably linked to the expression control sequence.

The invention also provides a method for identifying a compound affecting the activity or expression of the polynucleotide of claim 1, comprising the steps of:

(i) contacting a recombinant cell expressing the polynucleotide of the invention with a candidate material; and (ii) measuring an effect on the activity or expression of the polynucleotide.

The invention also provides an isolated polynucleotide encoding a polypeptide, wherein the polypeptide hybridizes to the nucleic acid sequence of SEQ ID NO: 1 or its complement, under high stringency conditions.

BRIEF DESCRIPTION OF THE DRAWINGS

The above and other objects, features and advantages of the present invention will be more apparent from the following detailed description taken in conjunction with the accompanying drawings, in which:

FIG. 1 shows the results of the multiple sequence alignment of the base sequences of a GmEXP1 gene and (α-expansin genes according to the present invention.

FIG. 4 is the Northern blot analysis results showing the expression patterns of the GmEXP1 gene according to the soybean organs. 25S rRNA is an internal control (A: leaf, B: stem, C: hypocotyl and D: root).

FIG. 7 is the Northern blot analysis results showing the expression patterns of the GmEXP1 gene in the primary and secondary roots of 5-day old soybean seedlings. 25S rRNA is an internal control (A: whole roots, B: primary root and C: secondary root).

FIG. 8 is the Northern blot analysis results showing the spatial expression patterns of the GmEXP1 gene in soybean roots. 25S rRNA is an internal control (A: diagram of sections of the whole root of 5-day old soybean, B: results of Northern blot performed on the sections of A, C: diagram of sections of the whole root of 9-day old soybean, D: results of Northern blot performed on the sections of C).

DETAILED DESCRIPTION OF THE INVENTION

Hereinafter, the present invention will be described with reference to the accompanying drawings.

To isolate new expansin genes, the inventors designed probes targeted to a common conserved region of generally known expansin genes and isolated one positive clone through investigation of a cDNA library of soybean. Upon analysis of the nucleotide sequence and amino acid sequence of the isolated clone, it was discovered that the cDNA isolated from soybean consists of 1,089 bp with an open reading frame encoding a polypeptide of 255 amino acids.

A gene isolated from soybean according to the present invention shows high-level of sequence homology to the group of α-expansins including tobacco, cucumber, rice and *Arabidopsis*, (See FIG. 1). Therefore, the inventors termed this gene "GmEXP1" and registered its nucleotide sequence with the GenBank (Accession No. AF516879). According to the phylogenetic classification, the GmEXP1 gene of the present invention belongs to Group D of the α-expansin subfamily (See FIG. 2).

Figure 3:
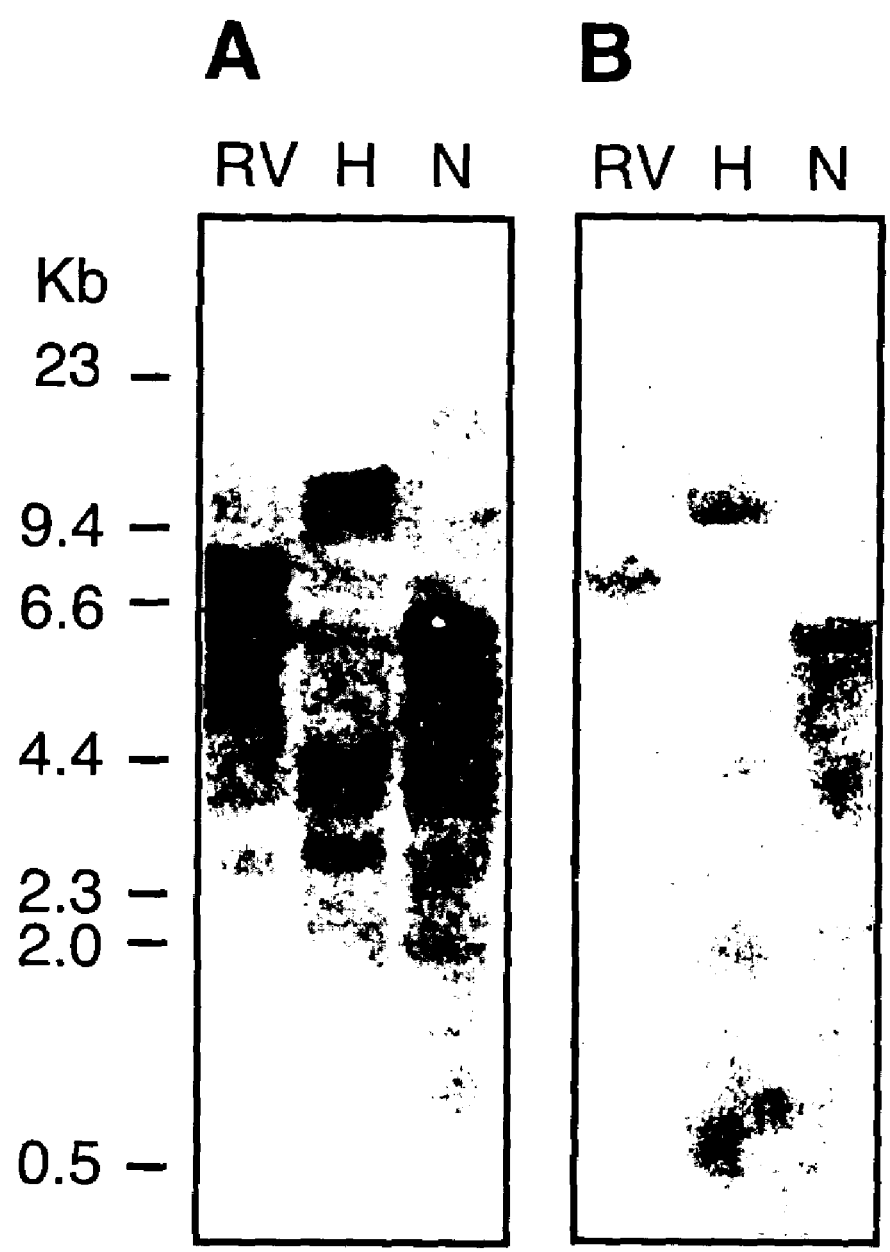
FIG. 3 shows the results of a Southern blot analysis of the GmEXP1 gene present in the soybean genome (A: hybridization with a probe containing only the coding region of the GmEXP1 gene, B: hybridization with a GmEXP1 gene-specific probe containing the coding region and the 3'-untranslated region of the GmEXP1 gene, RV: digested with EcoRV, H: digested with HindIII, N: digested with NcoI).

In one embodiment of the present invention, a Southern blot analysis was performed to confirm whether the GmEXP1 gene is actually present in the soybean genome. The analysis results show that a variety of expansins having homology to the α-expansin are present in the soybean genome, and that the GmEXP1 gene of the present invention is present in a single copy (See FIG. 3).

It is generally known that expansin genes are expressed in various regions of plants at different developmental stages. Most expansin transcripts are most abundant in actively growing organs, such as leaf primordia in tomato, internodes in rice, pollen in maize and soybean, pistil in tobacco, fruits in strawberry and tomato, and coleoptiles in oat, implying that the expansin genes are involved in critical developmental processes in plants.

Figure 5:
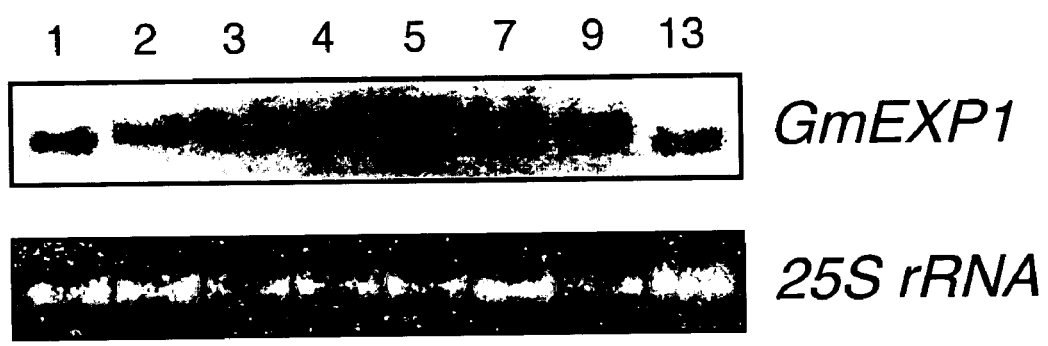
FIG. 5 is the Northern blot analysis results showing the expression patterns of the GmEXP1 gene at different developmental stages. 25S rRNA is an internal control.
Figure 6:
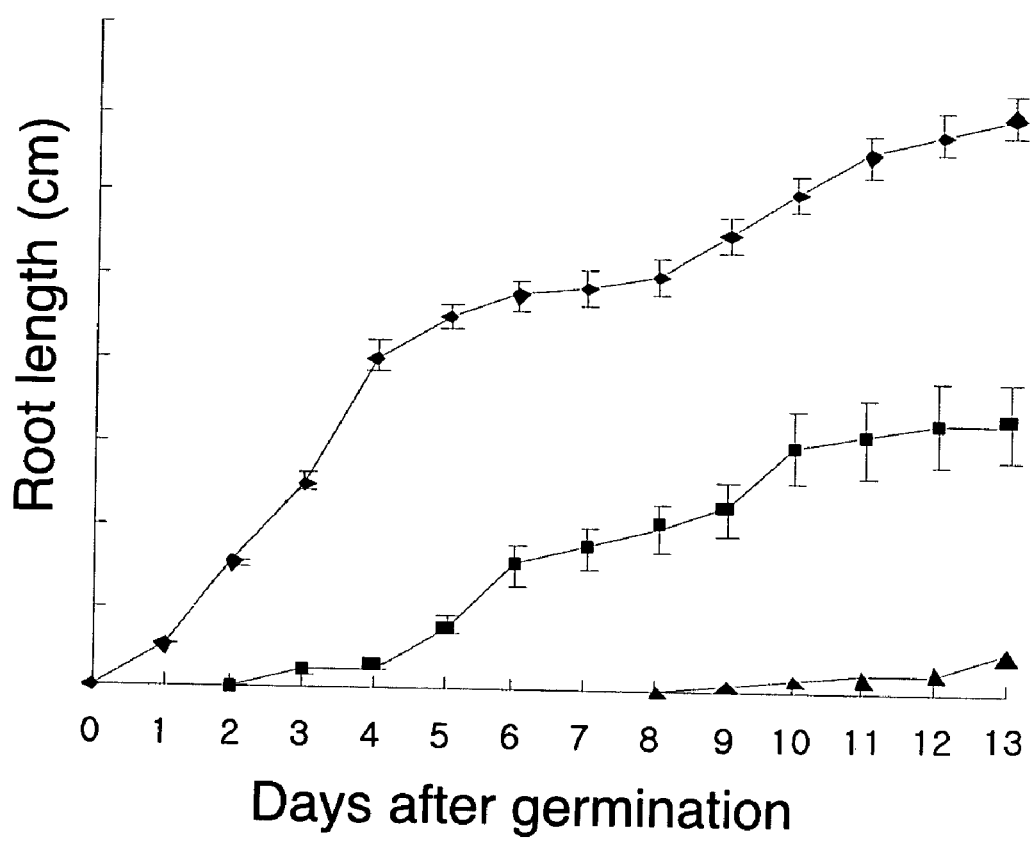
FIG. 6 is a graph showing the growth patterns of the primary, secondary and tertiary roots in soybean seedlings (♦: primary root, ■ : secondary root and ▲: tertiary root).

In another embodiment of the present invention, to investigate the expression patterns of the GmEXP1 gene in various organs of soybean, Northern blot analysis was preformed. The analysis results show that the GmEXP1 gene of the present invention is only expressed specifically in the soybean root (See FIG. 4). Based on the assumption that the GmEXP1 gene is closely related to the root growth of soybean, a Northern blot analysis was performed to detect the expression patterns of the GmEXP1 gene in roots at different developmental stages. It was revealed that the GmEXP1 gene is expressed in all developmental stages of the root (See FIG. 5) and the expression of the GmEXP1 gene is up-regulated particularly when soybean roots elongate rapidly (See FIG. 6 and FIG. 7).

Further, the spatial expression patterns of the GmEXP1 gene in soybean roots were analyzed in more detail by Northern blot and in situ hybridization. The results show that the GmEXP1 gene is highly expressed in the root tip involved in cell division and elongation in the primary and secondary roots. Also, the results show that the GmEXP1 gene is highly expressed in the secondary root initials emerging from the primary root. However, the GmEXP1 gene was not detected in the region where cell division had ceased (See FIG. 8).

Figure 9:
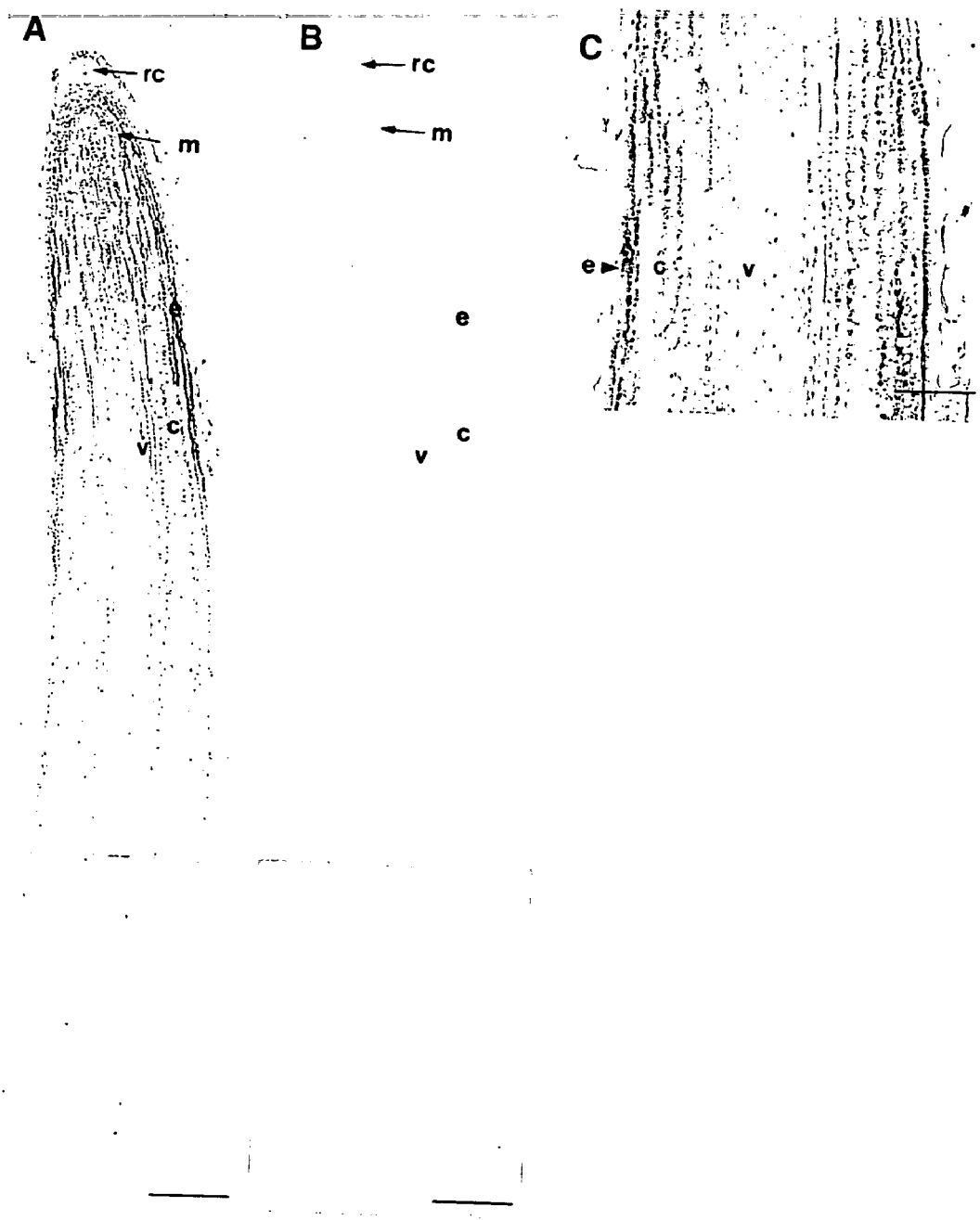
FIG. 9 is the in situ hybridization analysis results showing the spatial expression patterns of the GmEXP1 gene using longitudinal sections of the primary root of soybean (A: hybridization with the antisense probe for the GmEXP1 gene, B: hybridization with the sense probe for the GmEXP1 gene, C: enlarged image of the region of elongation in A, rc: root cap, e: epidermis, m: meristem, c: cortex, v: vascular cylinder, bars in A and B: 250 μm, bars in C: 100 μm).
Figure 10:
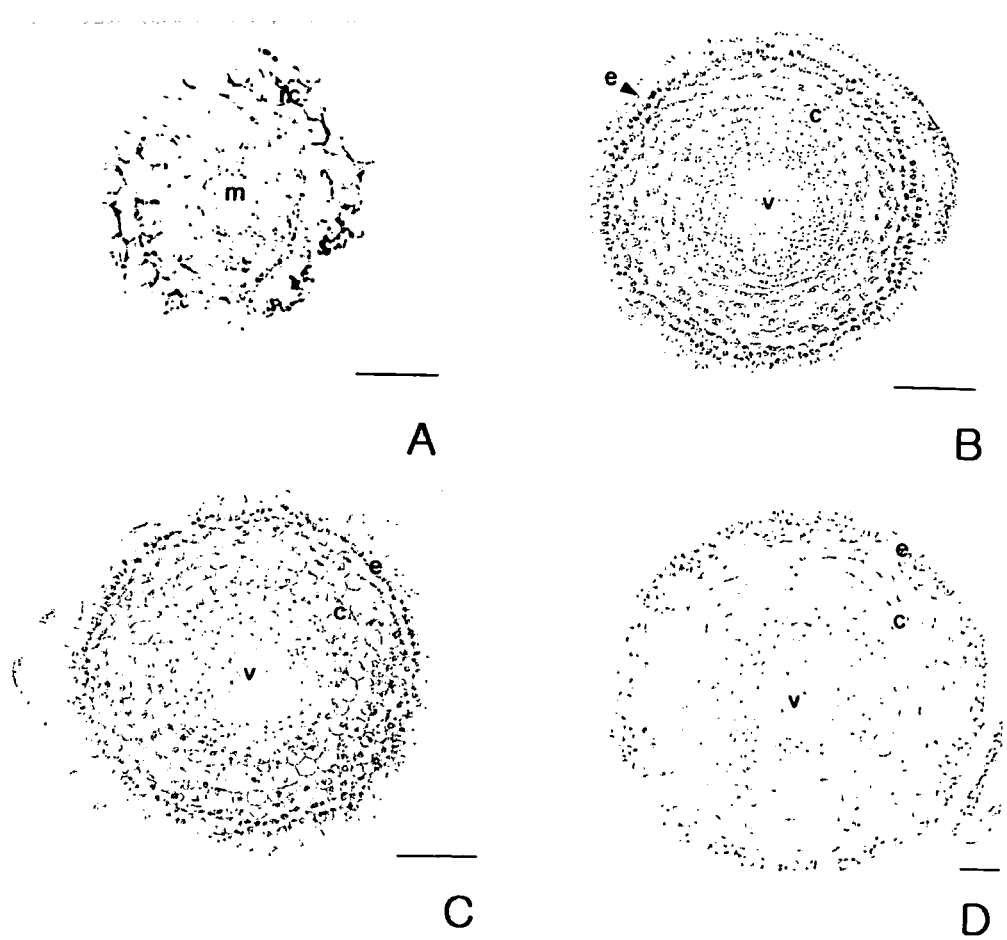
FIG. 10 is the in situ hybridization analysis results showing the spatial expression patterns of the GmEXP1 gene using cross sections of the primary root of soybean. (A: region that is 80 μm apart from the root tip, B: region that is 1.0 mm apart from the root tip, C: region that is 1.3 mm apart from the root tip, D: region that is 4.0 mm apart from the root tip, rc: root cap, e: epidermis, m: meristem, c: cortex, v: vascular cylinder, bars in A: 50 μm, bars in B, C and D: 100 μm).

According to the in situ hybridization, the GmEXP1 gene is expressed in the regions undergoing cell division and elongation in soybean roots and shows expression patterns specific to the epidermis and underlying cell layers of the region of elongation (See FIGS. 9 and 10). This suggests that the expression of gene according to the invention is related to the root development in the plant.

In still another embodiment of the present invention, in situ hybridization was conducted to identify the relationship between the GmEXP1 gene and the initiation of root formation and the role of the GmEXP1 gene in the root development of plants. It was revealed that the GmEXP1 gene is highly expressed in the epidermis of the primary and secondary root initials and in the tip region of the emerging secondary root (See FIG. 11). According to the analysis results, the GmEXP1 gene of the present invention is expressed in the root-specific pattern and plays an important role in the root growth of plants.

The inventors obtained transgenic plants overexpressing the GmEXP1 gene by transforming different species of plants with the GmEXP1 gene. In one example of the present invention, transgenic plants overexpressing the GmEXP1 gene were obtained by introducing the GmEXP1 gene into tobacco plants (*Nicotiana tabacum*) by *Agrobacterium tumefaciens*-mediated transformation. Also, the change of phenotypes of the transgenic plants was observed. It was observed that the transgenic plants overexpressing the GmEXP1 gene are relatively bigger than wild-type plants. The leaves and xylem cell layers in the stems of the transgenic plants were thicker than those of the wild-type plants (See FIG. 12). Also, the root tips of the transgenic plants were more elongated than those of the wild-type plants (See FIG. 13). It is clear that the GmEXP1 overexpression accelerates the root growth of plants.

Figure 14:
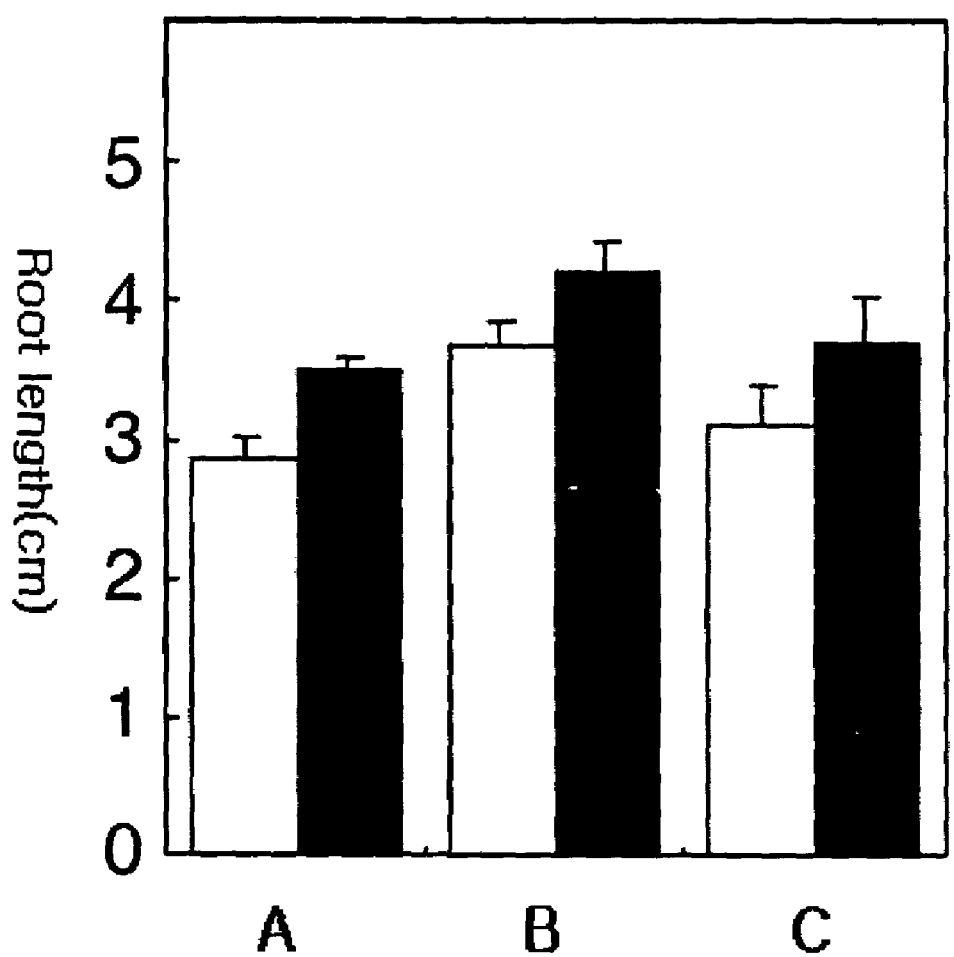
FIG. 14 is a graph comparing the length of wild-type tobacco root grown under acid condition with the length of transgenic tobacco root where the GmEXP1 gene is overexpressed (A: wild-type tobacco, B; transgenic tobacco, C: transgenic tobacco, □: pH 7.0, ■ :pH 4.5).

However, the expansin genes are known to have an activity regulated by various environmental stresses. For example, it was reported that low water potential increases the expansin activity (Wu et al., *Plant Physiol.*, 111:765–772, 1996). Thus, the inventors incubated transgenic plants with the GmEXP1 gene introduced thereto under both the neutral and acidic condition and compared the growth level of the transgenic plants with that of the wild-type plants. The transgenic plants overexpressing the GmEXP1 gene exhibited rapid root growth under both the neutral and acidic condition, as compared to the wild-type plants (See FIG. 14).

Figure 15:
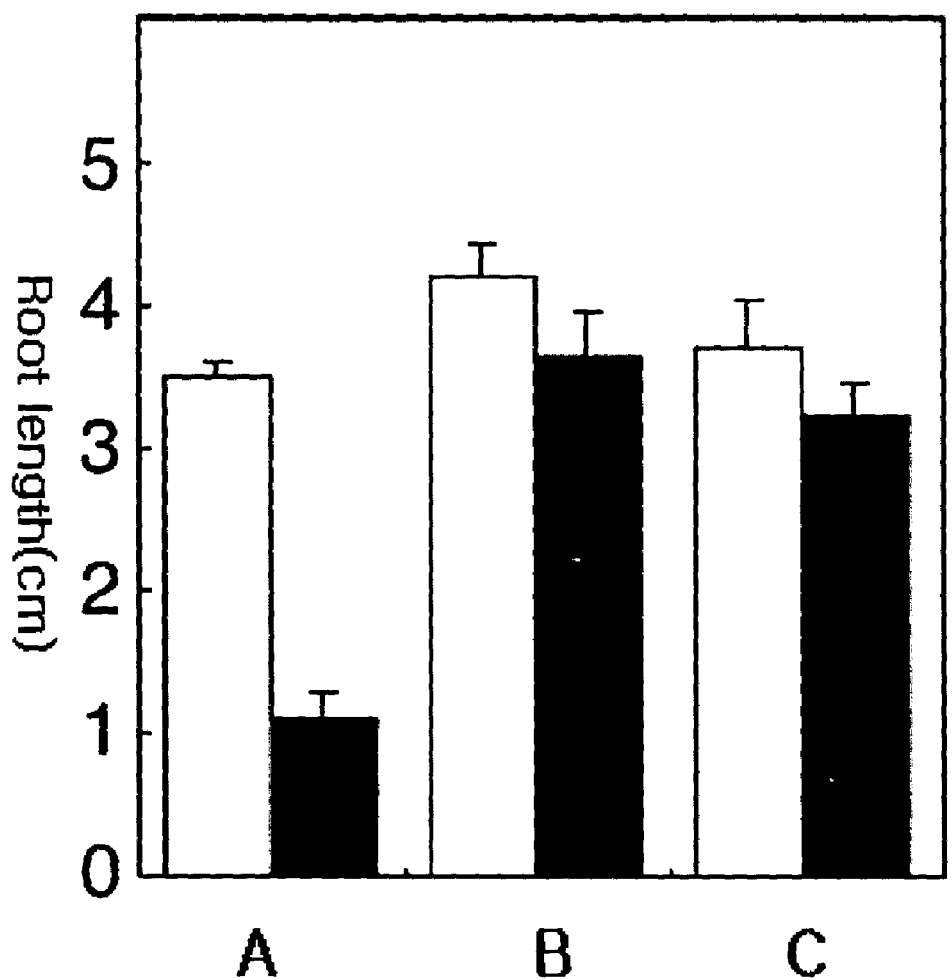
FIG. 15 is a graph comparing the length of wild-type tobacco root receiving the obstacle-touching stress with length of transgenic tobacco root where the GmEXP1 gene is overexpressed (A: wild-type tobacco, B; transgenic tobacco, C: transgenic tobacco, □: no obstacle-touching stress, ■ : obstacle-touching stress).

When plants are grown in soil, their roots may encounter obstacle-touching stress. Under obstacle-touching stress, the *Arabidopsis* roots begin to bend to realign themselves (Okada K. et al., *Science*, 250:274–276, 1990). In one embodiment of the present invention, the reaction of the transgenic plants overexpressing the GmEXP1 gene against the obstacle-touching stress was observed. The results show that the transgenic plants exhibited rapid root growth even under the obstacle-touching stress as compared to the wild-type plants, without showing any difference from the control plants, which were not under the obstacle-touching stress (See FIG. 15). This implies that the GmEXP1 overexpression provides the transgenic plants with insensitivity to the obstacle-touching stimulus, and that the gene plays an important role in overcoming the obstacle-touching stress when plants grow in soil.

In another embodiment of the present invention, which compares the epidermal cell length of the transgenic tobacco roots with that of the wild-type tobacco, it can be confirmed that the epidermal cells in the transgenic tobacco roots are longer than those in the wild-type tobacco roots. In transgenic plants overexpressing the GmEXP1 gene, root epidermal cells are rapidly elongated, thereby resulting in the rapid growth of the plants.

The present invention provides an isolated GmEXP1 polypeptide and polynucleotide encoding. The polypeptide according to the present invention includes a polypeptide comprising an amino acid sequence set forth in SEQ ID No. 2, and functional equivalents thereof.

The "functional equivalents" refer to polypeptide having more than 70%, preferably more than 80%, most preferably more than 90%, sequence homology to the amino acid sequence of SEQ ID No. 2 and exhibiting substantially the same physiological activity of the polypeptide of SEQ ID No. 2. Also, "substantially the same physiological activity" means an activity enhancing root growth of plants when a polypeptide is overexpressed in the plants.

The polypeptide according to the present invention can be obtained from nature (for example, plant cells) or by expression of a recombinant nucleic acid encoding the polypeptide or by a chemical synthesis. Preferably, the protein can be isolated from soybean.

Further, the present invention provides polynucleotides encoding the GmEXP 1 polypeptide. These polynucleotides include DNA, cDNA and RNA sequence which encode GmEXP 1 polypeptide. It is understood that all polynucleotides encoding GmEXP 1 are also included herein, as long as they encode a polypeptide with GmEXP1 activity. Such polynucleotides include naturally occurring, synthetic, and intentionally manipulated polynucleotides. The polynucleotide sequence for GmEXP 1 also includes antisense sequence. The antisense sequence is the polynucleotide encoding polypeptide, wherein the polypeptide hybridizes to the nucleic acid sequence of SEQ ID NO: 1 or its complement, under high stringency conditions Specially disclosed herein is a polynucleotide sequence containing the GmEXP 1 gene. Preferably, the polynucleotide sequence is SEQ ID NO: 1. The root growth control gene of the present invention has high homology to the genes which belong to the α-expansin subfamily. According to phylogenetic classification, the GmEXP1 gene of the present invention belongs to Group D of the α-expansin subfamily. The GmEXP1 gene is expressed in a root-specific manner and preferentially expressed in the regions of cell division and elongation of plant roots.

The polynucleotide sequence encoding GmEXP1 according to the present invention is inserted into a suitable expression vector to transform suitable host cells. The "host cells" are cells in which a vector can be propagated and its DNA expressed. The cell may be prokaryotic or eukaryotic. The "expression vector" refers to a known plasmid, virus or other vehicle known in the art that has been manipulated by insertion or incorporation of the GmEXP1 genetic sequences. The nucleic acid sequence of the present invention can be operably linked to the expression, control sequence. The operably linked nucleic acid sequence and expression control sequence can be included within a single expression vector containing a selective marker and a replication origin. The "operably linked" may mean that a nucleic acid sequence and an expression control sequence are linked in such a manner to enable expression of the nucleic acid. The "expression control sequence" refers to the nucleic acid sequence that regulates the expression of a nucleic acid sequence to which it is operably linked in a particular host cell. Such a control sequence includes promoters for performing transcription, operator sequences for controlling transcription, sequences encoding a suitable mRNA ribosome-binding site, and sequences controlling termination of transcription or translation. A suitable vector into which the GmEXP1 gene can be introduced is a Ti plasmid, a root inducing (Ri) plasmid or a plant virus vector. The most suitable vector may be, but not limited to, a binary vector of pPZP, pGA or pCAMBIA series. Anyone skilled in the pertinent art can select a suitable vector for introducing the nucleic acid of the present invention. Any vector capable of introducing the GmEXP1 gene sequence into plant cells can be used in the present invention. One example of the present invention describes a pGA643/GmEXP1 recombinant vector that introduces the GmEXP1 gene into pGA643 vector including CaMV 35S promoter.

The recombinant vector according to the present invention can be introduced into plant cells by known methods which include, but not limited to, transformation using *Agrobacterium* species, particle gun bombardment, silicon carbide whiskers, sonication, electroporation and PEG (polyethyleneglycol) precipitation.

The present invention also provides a method for enhancing root growth of plants using the GmEXP1 gene.

The present invention also provides a method for improving the resistance in plants against the obstacle-touching stress using the GmEXP1 gene.

More specifically, the present invention provides a method for enhancing root growth of plants or enhancing the resistance in plants to the obstacle-touching stress by overexpressing the GmEXP1 gene in the plants.

For overexpression, the GmEXP1 gene is introduced into plants with or without the GmEXP1 gene. The "overexpression" means the expression of the GmEXP1 gene at a level higher than that in wild-type plants. As a method for introducing a gene into a plant, there is a method for transforming a plant using an expression vector including the gene controlled by a promoter. Any promoter can be used if it can overexpress the gene introduced into the plant. The promoter may be, but not limited to, 35S RNA or 19S RNA promoter of CaMV, a full-length transcription promoter derived from Figwort mosaic virus (FMV), or a TMV coat protein promoter. Also, an ubiquitin promoter can be used to overexpress the gene in a monocotyledon or a woody plant.

The present invention is applicable to both monocotyledons and dicotyledons. The monocotyledons include, but not limited to, rice, wheat, barley, bamboo shoot, corn, taro, asparagus, onion, garlic, shallot, leek, yam and ginger. The dicotyledons include, but not limited to, *Arabidopsis*, eggplant, tobacco, cayenne, tomato, burdock, crown daisy, lettuce, Chinese bellflower, spinach, red beet, sweet potato, celery, carrot, parsley, Chinese cabbage, cabbage, leaf radish, watermelon, melon, cucumber, pumpkin, gourd, strawberry, soybean, mung bean, kidney bean and pea.

The GmEXP 1 polypeptide and polynucleotide encoding the polypeptide of the present invention can be utilized in the genetic improvement for root growth of plants and in the investigation of root growth regulating genes in other plants by known genetic engineering techniques, such as DNA chip, protein chip, polymerase chain reaction, Northern blot analysis, Southern blot analysis, enzyme-Linked Immunosorbent assay and 2-D gel analysis.

Also, the present invention provides a method for identifying materials influencing the activity of the polypeptide or the expression of the gene according to the present invention. More specifically, the present invention provides a method for identifying a compound influencing the activity of the polypeptide or the expression of the gene provided by the present invention, comprising the steps of contacting the polypeptide or a recombinant cell for expression of the polypeptide and a candidate material and measuring an effect on the activity of the polypeptide or the expression of the gene. The effect on activity or expression means enhancement of root growth and improvement of the resistance to the obstacle-touching stress by enhancing the activity of the polypeptide or the expression of the gene. The effect of a candidate material on the polypeptide or gene of the present invention can be evaluated by a known method such as Northern blot or Southern blot analysis. Compounds, which may affect the activity of the polypeptide or the expression of the gene of the present invention, include peptides, polypeptides, peptide copies, compounds and biologicals.

BEST MODE FOR CARRYING OUT THE INVENTION

This invention is further illustrated by the following examples, which are not be construed in any way as imposing limitations upon the scope thereof.

EXAMPLE 1

Cloning of Expansin Genes in Soybean (*Glycine max* cv *Paldal*) Roots

To isolate expansin cDNAs from soybean, primers targeted to the conserved regions of known expansin genes were designed, and PCR was carried out with soybean genomic DNA as a template. The conserved common regions of the expansin genes CsEXP1 (GenBank Accession No. U30382) and CsEXP2 (GenBank Accession No. U30460) of cucumber (*Cucumis*), the expansin gene AtEXP5 (GenBank Accession No. U30478) of *Arabidopsis*, the expansin genes OsEXP2 (GenBank Accession No. U30477) and OsEXP3 (GenBank Accession No. U30479) of rice (*Oryza*) and the expansin gene LeEXP1 (GenBank Accession No. U82123) of tomato (*Lycopersicon*) were analyzed using the website address at http://ncbi.nlm.nih.gov/Entrez/ and Clustal V software. To synthesize the conserved common regions of the above genes by PCR (polymerase chain reaction), two degenerate (forward and reverse) primers as mentioned below were synthesized.

```
Forward primer
                                          (SEQ ID No. 3)
5'-NNGGATCCGAYGCNTCNGGNACNATGGGYGGYGCTGYGYTANGG-3'

Reverse primer
                                          (SEQ ID No. 4)
5'-NNGGATCCTTKSWYTGCCARTTNNSNCCCCARTTNCK-3'
```

Wherein Y is T or C, K is T or G, S is C or G, and R is A or G.

PCR was carried out with soybean genomic cDNA as a template using the above primers. For 50 µl of a final reacting solution obtained by mixing 1×PCR buffer, 200 µM of each dNTP, 1 µM of each primer, 1.5 mM MgCl$_2$ and 2.5 units of Taq DNA polymerase (Bioneer, Daejon, Korea), PCR was performed at 94° C. for one minute, at 60° C. for one minute and at 72° C. for two minutes. The same reaction was repeated 35 times.

The amplified PCR product was isolated from a gel and purified by Geneclean II kit (BIO 101), and its nucleotide sequence was determined by the Sanger method (the dideoxynucleotide chain termination method)(Sanger F. T. et al., *Proc. Natl. Acad. Sci* USA, 74:5463, 1997). The amplified DNA fragments were labeled using the Prime-a-Gene system (Promega, Madison, Wis.) and used as a probe (SEQ ID No. 5) for screening expansin genes in the Uni-ZAP XR vector (Stratagene, La Jolla, Calif.) that is a cDNA library of soybean roots.

After screening the Uni-ZAP XR vector (Stratagene, La Jolla, Calif.) (Sambrook J. et al., *Molecular Cloning; A Laboratory Manual*, Ed. 2, Cold Spring Harbor Laboratory Press, Cold Spring Harbor, N.Y., 1989), one positive clone was isolated.

EXAMPLE 2

Determination of the Nucleotide Sequence of cDNA of Expansin Genes Isolated from Soybean Roots and Evaluation of Sequence Homology The nucleotide sequence of the clone isolated in Example 1 was determined by a kit (Sequence version 2.0 kit, USB) using the Sanger method. The determined DNA nucleotide sequence was analyzed using a sequence analysis program (Mac DNASIS program, Hitachi Software Engineering, America Ltd., San Bruno, Calif.), and an amino acid sequence was analogized from the base sequence. Also, the sequence homology between the nucleotide sequence of the expansin gene of the present invention and that of other known expansin genes was analyzed.

As a result, it was revealed that the isolated cDNA consists of 1,089 bp with an open reading frame encoding a polypeptide of 255 amino acids, which contains a putative signal sequence of 16 amino acids at the N terminus. Also, the homology analysis showed that the gene of the present invention has strong sequence similarities to a group of α-expansins including NtEXP3 of tobacco (86%; Link B. M. et al., *Plant Physiol.*, 118:907–916, 1998), CsEXP2 of cucumber (92%; Shcherban T. Y. et al., *Proc. Natl. Acad. Sci.*, USA, 92:9245–9249, 1995), OsEXP1 of rice (85%; Cho H-T t al., *Plant Cell*, 9:1661–1671, 1997b) and AtEXP1 of *Arabidopsis*(82%; Shcherban T.Y. et al., *Proc. Natl. Acad. Sci.*, USA, 92:9245–9249, 1995) (See FIG. 1). Thus, the inventors termed the new expansin gene isolated from the soybean root "GmEXP1". The nucleotide sequence and amino acid sequence of the GmEXP1 gene are shown in SEQ ID No. 1 and SEQ ID No. 2.

EXAMPLE 3

Phylogenetic Classification of GmEXP1

The GmEXP1 gene having high-level homology to the α-expansin genes was classified by a phylogenetic analysis. The phylogenetic tree for 20 known α-expansin genes and the expansin gene of the present invention was constructed by the maximum likelihood method (HKY 85 model) using PAUP program. Known α-expansin genes as used in this example are AtEXP6 (GenBank Accession No. U30480), AtEXP1 (GenBank Accession No. U30476), AtEXP (GenBank Accession No. U30478) and AtEXP2 (GenBank Accession No. U30481) derived from *Arabidopsis(Arabidopsis thaliana)*; PsEXP1 (GenBank Accession No. 85187) derived from pea (*Pisum sativum*); LeEXP1 (GenBank Accession No. U82123), LeEXP18 (GenBank Accession No. AJ004997) and LeEXP2 (GenBank Accession No. AF096776) derived from tomato (*Lycopersicon esculentum*); NtEXP4 (GenBank Accession No. AF049353), NtEXP5 (GenBank Accession No. AF049354), NtEXP1 (GenBank Accession No. AF049350), NtEXP2 (GenBank Accession No. AF49351) and NtEXP3 (GenBank Accession No. AF049352) derived from tobacco (*Nicotiana tabacum*); PtEXP1 (GenBank Accession No. U64892) derived from loblolly pine (*Pinus taeda*); CsEXP2 (GenBank Accession No. U30477) derived from cucumber (*Cucumis sativus*); OsEXP1 (GenBank Accession No. Y07782), OsEXP 2 (GenBank Accession No. U30477), OsEXP3 (GenBank Accession No. U30479) and OsEXP4 (GenBank Accession No. U85246) derived from rice (*Oryza sativa*); and PHLP1 (GenBank Accession No. X78813) derived from timothygrass (*Phleum pratense*).

Figure 2:
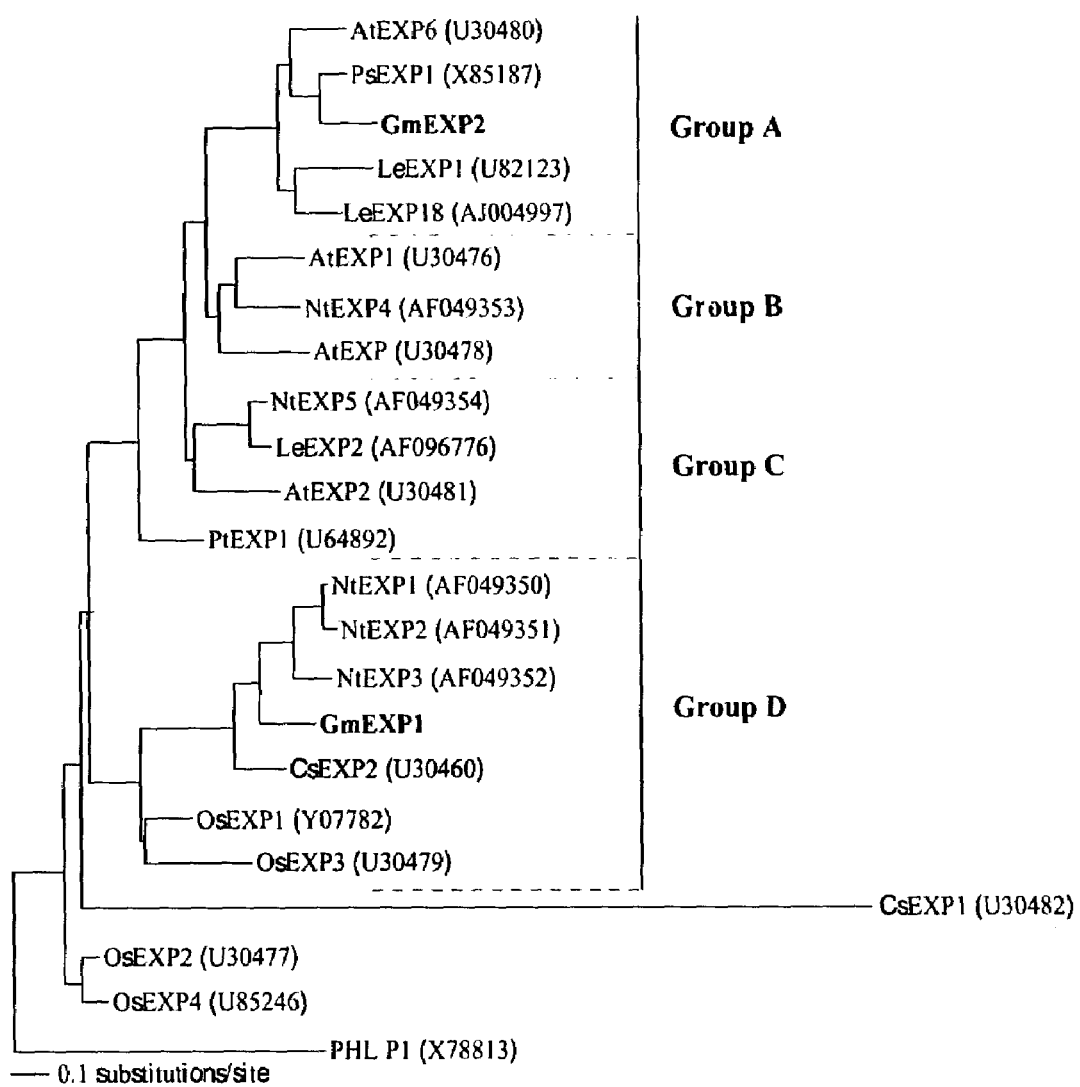
FIG. 2 is a phylogenetic profile of the GmEXP1 gene according to the present invention.

The analysis results show that the GmEXP1 gene of the present invention belongs to Group D of the α-expansin subfamily (See FIG. 2).

EXAMPLE 4

Analysis of GmEXP1 Gene Present in Soybean Genome

To estimate the presence and number of the GmEXP1 gene in the soybean genome, a Southern blot analysis was performed with part of the GmEXP1 gene as a probe. A genomic DNA was isolated from leaves of soybean grown in a Hoagland solution for 20 days under long-day condition (16-hour light/8-hour dark) at 26° C., utilizing DNeasy Plant Mini Kit (QIAGENE®). 10 µg of the extracted DNA was digested with different restriction enzymes EcoRV, HindIII and NcoI. The digested DNA is separated in a 1% agarose gel and transferred onto a Hybond N$^+$ nylon membrane (Amersham Biosciences AB, Uppsala). A Southern blot analysis was performed with the DNA fragments (nucleic acid Nos. 52 to 816 of GmEXP1) containing the coding region of GmEXP1 or the DNA fragments (nucleic acid Nos. 603 to 991 of GmEXP1) containing the coding region and the 3'-untranslated region of GmEXP1 as a probe. The probe was labeled with the radioactive isotope a$^{-32}$P and hybridized with the nylon membrane, to which the genomic DNA is attached, at 65° C. (Ahn J.H. et al., *Plant Physiol.*, 116:671–679, 1998). For quantification, the membrane was analyzed with a bioimaging analyzer (BAS-1500, Fuji, Tokyo, Japan)

As a result, in the case of the hybridization with only the coding region of the GmEXP1 cDNA, many bands were detected in each lane (See FIG. 3-A), implying that various expansin genes with homology to the α-expansins are present in the soybean genome. However, when a probe specific only for the GmEXP1 gene including both the coding region and the 3'-untranslated region was used in hybridization, a strong single band appeared along with occasional weaker bands in each blot (See FIG. 3-B). It suggests that the GmEXP1 gene exists as a single-copy gene in the soybean genome.

EXAMPLE 5

Expression Patterns of GmEXP1 in Different Tissues of Soybean

The expression patterns of the GmEXP1 gene were investigated in different tissues of soybean. Total RNAs were isolated from the leaves, roots, stems and hypocotyls of soybean seedlings grown for 20, days under the same condition as used in Example 4. Northern blot analysis was performed with a GmEXP1 -specific probe. RNeasy Plant Kit (QIAGENE®) was used to isolate the RNAs from different tissues. 10 μg of the isolated RNA was separated in a 1% agarose gel containing formaldehyde, transferred onto a nylon membrane, and hybridized with the probe at 65° C. For quantification, the membrane was analyzed with a bioimaging analyzer (BAS-1500, Fuji, Tokyo, Japan).

As a result, hybridization signals were detected only in the RNA isolated from roots (See FIG. 4), indicating that the GmEXP1 gene is root-specific and may be involved in root development. The size of the GmEXP1 mRNA was about 1.1 kb, which is similar to that predicted from its cDNA sequence.

EXAMPLE 6

Expression Patterns of GmEXP1 in Soybean Roots at Different Developmental Stages The expression patterns of the GmEXP1 gene were evaluated in soybean roots at different developmental stages by the same method as used in Example 5. Total RNAs were extracted from roots of 1-, 2-, 3-, 4-, 5-, 7-, 9- and 13-day old soybean seedlings. Northern blotting was performed with a GmEXP1 -specific probe by the same method as used in Example 5.

The growth pattern of soybean roots was compared with the expression pattern of the GmEXP1 gene. The growth pattern of soybean roots was monitored by measuring the root lengths of the primary, secondary and tertiary roots of six young seedlings grown in a liquid medium. The expression pattern of the GmEXP1 gene was detected by isolating RNAs from the primary and secondary roots 5 days after germination, using Northern blot analysis.

As a result, the GmEXP1 gene was expressed in all root developmental stages. Particularly, the expression level was very high 1 day after germination and reached the maximum level 5 days after germination (See FIG. 5).

The primary roots grew rapidly until 4 days after germination, and then their growth rate was gradually decelerated. The secondary roots were initiated from the primary root 2 days after germination and grew rapidly from 4 to 6 days after germination. The tertiary roots emerged 8 days after germination (See FIG. 6). Although the GmEXP1 gene was expressed in both the primary roots and the secondary roots of 5-day old seedlings, the expression level was much higher in the secondary roots (See FIG. 7). This is probably because the growth of the primary roots was decelerated from $5^{th}$ day of germination, whereas the growth of the secondary roots was accelerated. Furthermore, the expression levels of the GmEXP1 gene were gradually decreased as the growth of the secondary roots was decelerated. Therefore, it suggests that the GmEXP1 gene is involved in root development and that the expression of the GmEXP1 gene is up-regulated when rapid root elongation takes place during root development in soybean.

EXAMPLE 7

Spatial Expression Patterns of GmEXP1 in Soybean Roots

The spatial expression patterns of the GmEXP1 gene were analyzed by Northern blot and in situ hybridization. That is, the expressions of the GmEXP1 gene in the 5-day-old primary roots and 9-day-old seedlings that showed the maximum level of GmEXP1 expression were determined.

7-1) Northern Blot

The primary roots were serially dissected into 8 sections (FIG. 8-A), and the secondary roots were serially dissected into 5 sections (FIG. 8-C). Total RNAs were isolated from each section and subjected to a Northern blot analysis by the same method as used in Example 5.

As a result, the GmEXP1 transcripts were predominantly detected in section 1 of the primary roots, representing the root tip region of cell division and elongation (Ahn J. H. et al., *Plant Physiol.*, 116:671–679, 1998). In contrast, the expression level was very low in sections 2 to 8 (See FIG. 8-B). Interestingly, a slightly elevated level of the GmEXP1 expression was detected in section 6, which was most likely contributed by the emerging secondary roots. Even in the secondary roots, the expression level was high in section 1 that includes the tip region (See FIG. 8-D). Therefore, it is concluded that the GmEXP1 gene is highly expressed in a specific zone that includes the region of cell division and elongation in the primary and secondary roots, and that the GmEXP1 gene plays an important role in cell elongation during root development.

7-2) In Situ Hybridization

In situ hybridization was used to detect the regions where the GmEXP1 gene is expressed. The hybridization was performed using the primary roots of 5-day old soybean seedlings by modifying a known method (Glik B.R. et al., *Methods in Plant Molecular Biology and Biotechnology*, CRC Press, 179–205, 1993; Cho H-T et al., *Plant J*, 15:805–812, 1998). The primary roots of the soybean seedlings were immediately immersed in the formaldehyde-acetic acid-fixation solution containing 50% (v/v) ethanol, 5% (v/v) acetic acid and 3.7% (v/v) formaldehyde, and the tissues were subsequently fixed and embedded in paraplast. The embedded root tissues were vertically or horizontally sliced into 8-μm thick sections using a microtome (Leica Instruments GmbH, Wetzlar, Germany). When the roots were horizontally cut, sections were selectively obtained from the regions of cell division, elongation and maturation based on the anatomical features. For the in situ hybridization, a probe synthesizing a DIG-labeled RNA probe (antisense: SEQ ID No. 6 or sense: SEQ ID No. 7) with the GmEXP1 -specific DNA fragments in Example 4 as a template was used. That is, the GmEXP1-specific DNA fragments were digested with EcoRV, HindIII and NcoI and inserted into the pSTP18 vector (Roche Diagnostics, Manheim, Germany). The RNAs were obtained using SP6 or T7 polymerase with the plasmid as a template. The RNAs are in the form of a mixture of digoxigenin and UTP. The sense probe was used as the control group. The synthesized DIG-labeled RNA probe was hybridized with the soybean root tissue fragments at 65° C., and reacted with $1^{st}$ DIG antibody (Boehringer Manheim) which specifically reacts to digoxigenin labeled with alkaline phosphatase. Upon completion of the reaction, the resulting product was dyed with nitroblue tetrazolium/5-bromo-4-chloro-3-indolylphosphate and observed using a microscope (Optiphot-2, Nikon, Tokyo).

The results of in situ hybridization were identical to those obtained by RNA genome gel blot in Example 7-1). The GmEXP1 gene was highly expressed in the root tip region of the primary roots of soybean seedlings. When longitudinal sections of the primary roots were hybridized with an antisense probe, the expression levels of the GmEXP1 gene gradually increased from the region of cell division to the region of elongation and then decreased in the region of maturation (See FIG. 9-A). In case of hybridization with a sense RNA probe, no expression of the GmEXP1 gene was detected (See FIG. 9-B). The elongation region of the primary root, which was hybridized with the antisense RNA probe, was observed upon magnification. It was detected that the GmEXP1 gene was highly expressed in the epidermis, some underlying cell layers and the vascular cylinder in the region of elongation (See FIG. 9-C). Also, in the cross sections of the primary roots of the soybean seedlings, the GmEXP1 gene showed low expression level at the cells in the root cap (See FIG. 10-A) and a high expression level at cells of epidermis and vascular cylinder in the region of elongation (See FIGS. 10-B and 10-C). However, the GmEXP1 gene showed low-level expression at the epidermal cells in the maturation region (See FIG. 10-D). These results imply that the GmEXP1 gene is expressed in the regions of cell division and elongation, preferentially in their epidermal cells and some underlying cell layers.

EXAMPLE 8

Relationship Between GmEXP1 Expression and Root Initiation

To test whether GmEXP1 gene is involved in formation of the root initials, the expression patterns of the GmEXP1 gene were investigated in the secondary root initials. The secondary root-initiating region in the primary root of 5-day old soybean seedlings (about 3.5 cm from the root tip) was longitudinally or horizontally sectioned and subjected to in situ hybridization analysis. In situ hybridization was performed using a sense RNA probe or an antisense RNA probe in the same manner as described in Example 7-2).

Figure 11:
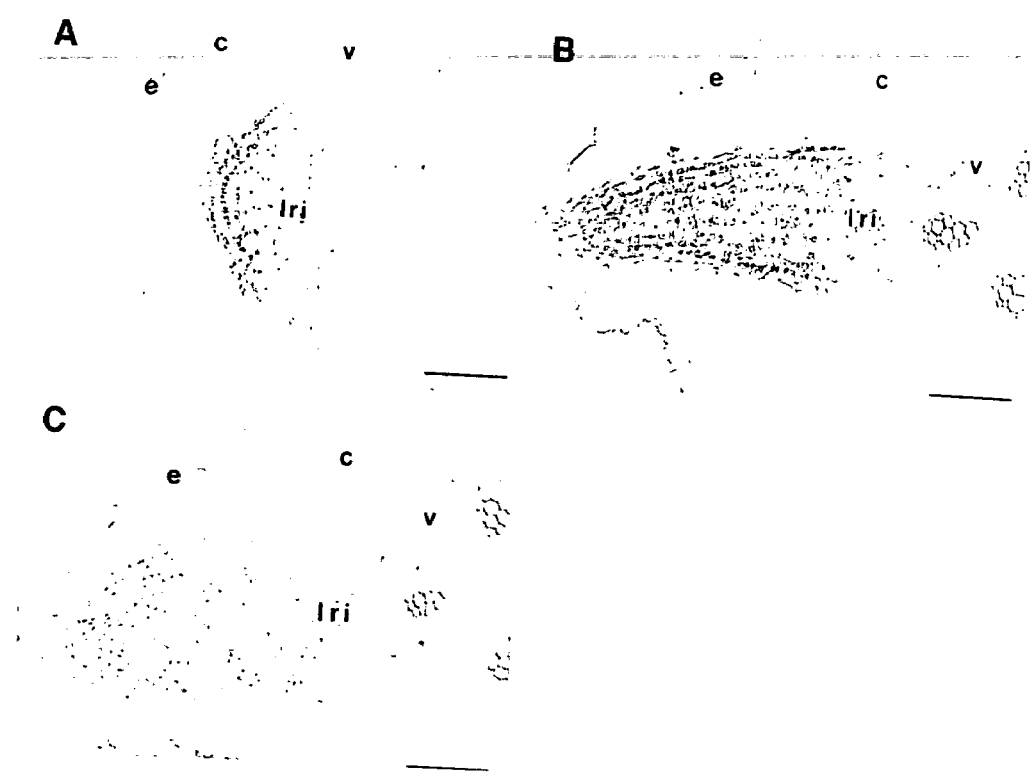
FIG. 11 is the in situ hybridization analysis results showing the expression patterns of the GmEXP1 gene at the secondary root initiating stage (A: longitudinal section hybridized with the antisense probe, B: cross section hybridized with the antisense probe, C: cross section hybridized with the sense probe, lri: secondary root initial, e: epidermis, v: vascular cylinder, c: cortex, bars: 100 μm).

As a result, it was detected that the GmEXP1 gene was expressed in the secondary root initials, particularly in their epidermal cells (See FIG. 11-A). In the cross sections of the primary root hybridized with an antisense RNA probe, the GmEXP1 gene was mainly expressed in the tip region of the emerging secondary root (See FIG. 11-B). In contrast, the sections hybridized with a sense probe did not show any detectable expression of the GmEXP1 gene (See FIG. 11-C). It is known that the secondary root is initiated from the pericycle in the region of maturation of the primary root and then penetrates through the cell layers of cortex and epidermis to emerge from the primary root (Malamy J. E. et al., *Development*, 124:33–44, 1997). Although the origin of the secondary root is different from that of the primary root, they commonly require the GmEXP1 gene for cell elongation and have no significant difference in their morphology, organization or gene expression (Dolan L. et al., *Development*, 119:71–84, 1993).

EXAMPLE 9

Reaction of Tobacco Transformed with GmEXP1 in Acidic Condition and Insensitivity to Obstacle-Touching Stress 9-1) Transformation of Tobacco The GmEXP1 gene was overexpressed in tobacco plants in order to identify the function of the gene in plants. For amplification of the coding region (765 bp) of the GmEXP1 cDNA, a pair of primers as mentioned below was synthesized by a known method.

Forward primer
5'-ACCAAGCTTCAACCTCTCATCATTAGGC-3'   (SEQ ID No. 8)

Reverse primer
5'-ACCAAGCTTGGAGTTGATGGGAATAATCA-3'   (SEQ ID No. 9)

PCR was carried out with soybean cDNA library (Uni-ZAP XR vector) as a template using the above primers. The PCR-amplified product was digested with HindIII and then inserted into the HindIII site of the pGA643 vector containing the CaMV 35S promoter and NOS terminator (An G. et al., *Binary Vectors*, Plant Molecular Biology Manual, Kluwer Academic Publishers, A31–A319). The vector was introduced into *Agrobacterium tumefaciens* cells by electroporation. *A. tumefaciens*-mediated tobacco plants transformation was performed as a known method (Holsters M. et al., *Mol. Gen. Genet.*, 163:181–187, 1978; Horsch R.B. et al., *Science*, 227:1229–1231, 1985). The transformed (transgenic) tobacco plants were cultured and selected on Murashige and Skoog basal medium supplemented with 200 mg/L of kanamycin and 500 mg/L of carbenicillin.

9-2) Change in the Phenotype of Transgenic Tobacco

The phenotype of the transgenic tobacco plants obtained in Example 9-1) was compared with that of the wild-type tobacco plants. Also, the transgenic plants with overexpressed GmEXP1 gene were dissected in the same manner as described in Example 7-2) and the anatomical features of the transgenic plants were observed by a microscope.

Figure 12:
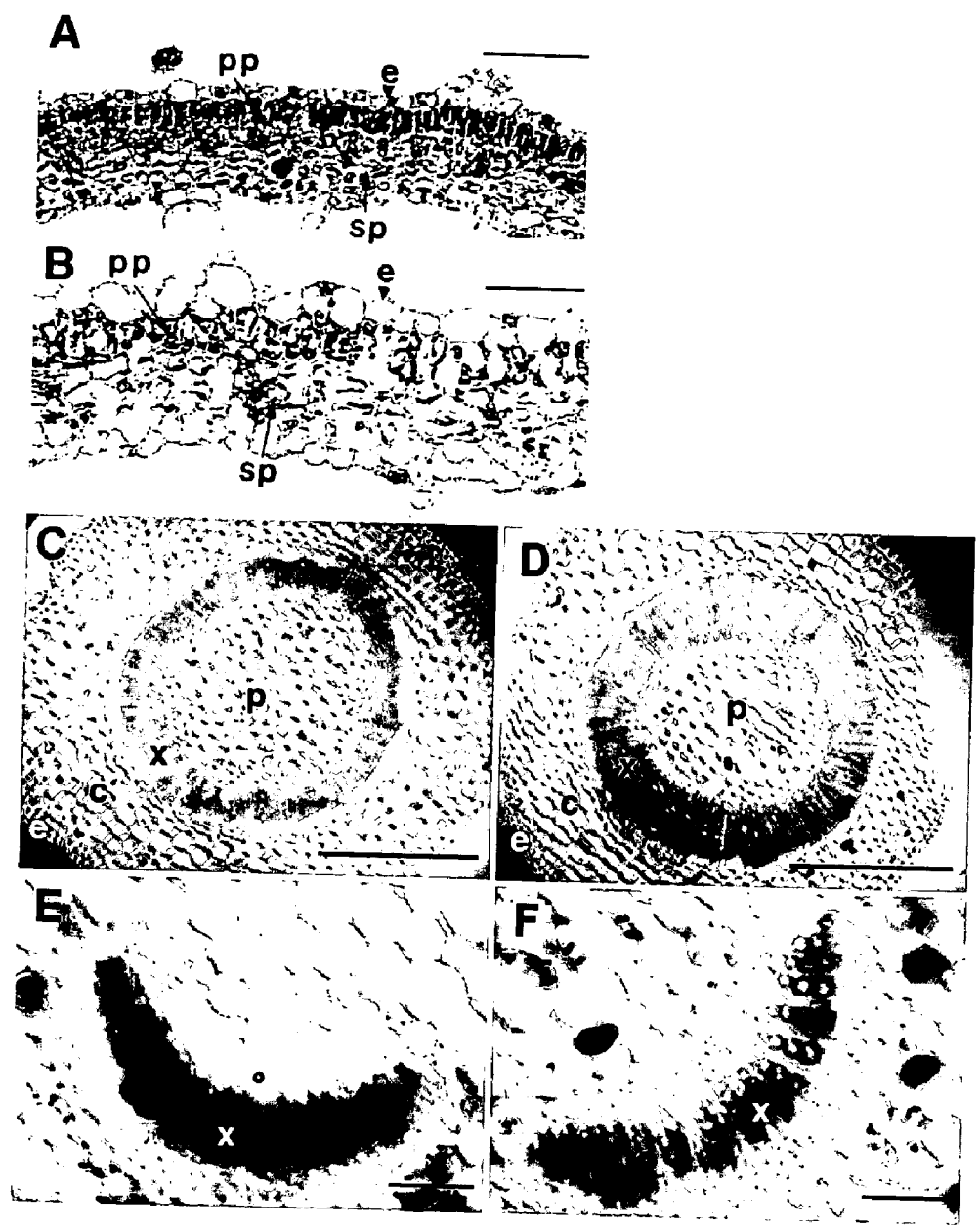
FIG. 12 shows the anatomical features of transgenic tobacco plants overexpressing the GmEXP1 gene, which are observed by a microscope (A: cross section of a leaf of wild-type tobacco, B: cross section of a leaf of transgenic tobacco, C: cross section of the stem of wild-type tobacco, D: cross section of the stem of transgenic tobacco, E: cross section of the petiole of wild-type tobacco, F: cross section of the petiole of transgenic tobacco, e: epidermis, pp: palisade parenchyma, sp: spongy parenchyma, c: cortex, x: xylem, p: pitch, bars in A and B: 300 μm, bars in C and D: 1000 μm, bars in E and F: 100 μm).
Figure 13:
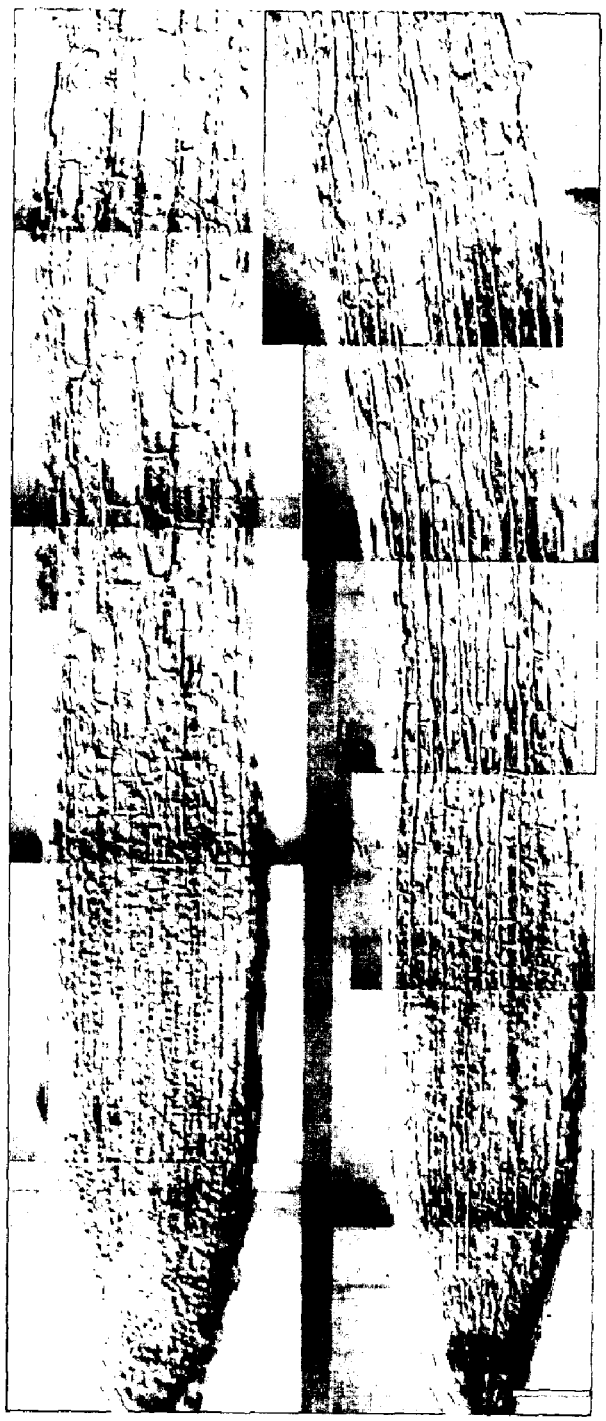
FIG. 13 shows the root apical region of transgenic tobacco plants overexpressing the GmEXP1 gene, which are observed by a microscope (left: wild-type tobacco, right: transgenic tobacco, bars: 100 μm).

The transgenic plants with overexpressed GmEXP1 gene were relatively bigger than the wild-type plants. This suggests that the overexpression of the GmEXP1 gene accelerates the growth of plants. In addition, abnormal phenotypes were detected in the leaves, stems and flowers of the transgenic plants. The strong lines at which the GmEXP1 gene was highly expressed showed a bushy phenotype, because multiple leaves developed simultaneously from the shoot apex. In contrast, the weak lines at which the GmEXP1 gene showed low-level expression showed a phenotype generating auxiliary shoots, probably due to weak apical dominance (data not shown). In terms of anatomical features, the cells in the leaves of the strong lines were enlarged and layered irregularly (See FIGS. 12-A and 12-B). Also, the transgenic plants showed thickened xylem cell layers in the stems (FIGS. 12-C and 12-D), although there was no significant difference in xylem cells of the petioles of the transgenic plants as compared to those of the wild-type plants (FIGS. 12-E and 12-F). It was also detected that the root tip region of the transgenic plants was more elongated than that of the wild-type plants. The analysis results indicate that the overexpression of the GmEXP1 gene accelerates the growth of plants and selectively affects developmental processes of transgenic plants.

9-3) Growth Rate of Transgenic Plants in Acidic Condition and Sensitivity to Obstacle-Touching Stress In order to observe the growth rate of transgenic tobacco roots under acidic condition, the transgenic tobacco plants with low expression level of the GmEXP1 gene were self-pollinated to obtain homozygous seeds in the $T_2$ generation, because transgenic plants with a high expression level of the GmEXP1 gene are sterile. The $T_2$ seeds were sterilized with 10% (w/v) bleach solution for 10 minutes and washed several times with sterile water. The seeds were sown on 1.5% (w/v) agar plates containing 0.5 x Murashige and Skoog basal medium (Invitrogen, Carlsbad, Calif.) and which are adjusted to pH 4.5 or 7.0. As a control group, wild-type soybean seeds were sown on the agar plates in the same manner. The homozygous transgenic seeds and the wild-type seeds were incubated on the plates vernalized by cold treatment (for 2 days in the dark) in a vertical position under long-day condition (16-hour light/8-hour dark) at 26° C. The lengths of their primary roots were measured 17 days after germination.

As a result, it was detected that the primary roots of the transgenic seedlings are longer than those of the wild-type seedlings under both neutral and acidic conditions. Particularly, transgenic seedlings grown under acidic condition had longer root length than those grown under neural condition (See FIG. 14). It is known that the acidic condition accelerates the growth of plant tissues. The transgenic seedlings with overexpressed GmEXP1 gene appear to have been more reactive in the acidic condition, thereby having longer roots than the wild-type seedlings. These data suggest that the GmEXP1 gene induces acid growth in soybean.

Also, in order to investigate the resistance (insensitivity) of the transgenic tobacco roots to the obstacle-touching stress, the $T_2$ seeds and the wild-type seeds were sterilized and incubated on pH 4.5 agar plates containing the MS medium in the same manner as described above. After vernalization (cold treatment) for 2 days, the plates were erected in a vertical position(90°). On the 3rd day, one half of the plates were inclined at 45° to give the obstacle-touching stress, and the rest were continually incubated in a vertical position. The seeds were incubated under long-day condition (16-hour light/8-hour dark) at 26° C. The lengths of their primary roots were measured 17 days after germination.

As a result, in the vertical plates, the primary roots of the wild-type soybean seedlings, which did not encounter the obstacle-touching stress, just grew straight downward on the surface of the agar. In contrast, the primary roots of the wild-type seedlings, which were affected by the obstacle-touching stress, were much shorter. The average root length was 3.5 cm under no obstacle-touching stress. The root length was reduced to 1.1 cm under the obstacle-touching stress. However, the primary roots of GmEXP1 overexpressing seedlings were barely affected by the obstacle-touching stress and much longer than those of the wild-type seedlings (See FIG. 15). From these results, it is clear that the GmEXP1 overexpression improves the resistance to the obstacle-touching stress, and that the GmEXP1 gene plays an important role in overcoming the stress, which the primary roots would encounter in soil.

9-4) Length of Root Epidermal Cells in Transgenic Seedlings

Wild-type and homozygous transgenic seeds were incubated on 1 50 o (w/v) agar plates (pH 4.5) in an inclined position at 45° C. to encounter the obstacle-touching stress. The seeds were incubated under long-day condition (16-hour light/8-hour dark) at 26° C. The lengths of the epidermal cells in their roots and stems were measured 17 days after germination. The cell length was measured using the NIH image software (developed by the United States National Institute of Health and available on the Internet at rsb.info.nih.gov/nihimage).

As shown in Table 1, when compared to the roots of the wild-type seedlings, the roots of the transgenic seedlings overexpressing the GmEXP1 gene showed significant elongation of epidermal cells, which is likely to be a main reason for the rapid growth. However, there was no significant difference in the epidermal cell length in stems and vascular cylinder between the transgenic roots and the wild-type roots (data not shown)

TABLE 1

Comparison of Length of Root Epidermal Cells

| Distance from | Cell Length | |
| --- | --- | --- |
| Root Tip | Wild Type Soybean | Transgenic Soybean |
| 400 | 17.6 ± 3.9 | 30.2 ± 6.9 |
| 800 | 32.0 ± 5.0 | 71.9 ± 15.7 |
| 1,200 | 140.5 ± 21.6 | 216.0 ± 25.5 |
| 1,600 | 188.7 ± 33.7 | 207.9 ± 30.7 |

The GmEXP1 gene of the present invention and the expansin protein expressed from the GmEXP1 gene can be utilized in the genetic improvement for root growth of plants and in the investigation of root growth regulating genes in other plants. Also, the GmEXP1 gene plays important roles in accelerating root development of plants and overcoming the obstacle-touching stress.

Although some working examples of the present invention have been described for illustrative purposes, those skilled in the art will appreciate that various modifications, additions and substitutions are possible, without departing from the scope and spirit of the invention as disclosed in the accompanying claims.

The entire disclosure of Korea Patent Application No. 2003-19069, filed on Mar. 27, 2003 including its specification, claims, drawings and summary are incorporated herein by reference in its entirety.

What is claimed is:

1. An isolated polynucleotide encoding a root growth regulating polypeptide, wherein the polypeptide comprises the amino acid sequence set forth in SEQ ID NO: 2 or the amino acid sequence with at least 90% sequence homology to SEQ ID NO: 2.

2. The polynucleotide of claim 1, having the nucleic acid sequence set forth in SEQ ID NO: 1.

3. The polynucleotide of claim 1, having a root-specific expression pattern when present in the native genome.

4. A recombinant vector comprising the polynucleotide of claim 1.

5. A cell comprising the isolated polynucleotide of claim 1.

6. A plant comprising the isolated polynucleotide of claim 1.

7. A plant tissue or seed comprising the isolated polynucleotide of claim 1.

8. A method for enhancing root growth of a plant, comprising the steps of: i) introducing the polynucleotide of claim 1 into a plant cell to obtain a transformed plant cell, wherein the polynucleotide is operably linked to an expression control sequence; ii) producing a transformed plant from said transformed plant cell; and iii) selecting a transformed plant exhibiting rapid root growth compared to a plant which was not introduced with the polynucleotide under neutral and acidic conditions.

9. The method of claim 8, wherein the plant cell is selected from the group consisting of protoplasts, gamete producing cells and cells which regenerate into a whole plant.

10. The method of claim 8, wherein the plant cell is monocotyledon or dicotyledon.

11. A method for enhancing resistance in a plant to obstacle-touching stress, comprising the steps of:
  i) introducing the polynucleotide of claim 1 into a plant cell to obtain a transformed plant cell, wherein the polynucleotide is operably linked to an expression control sequence;
  ii) producing a plant from said transformed plant cell; and
  iii) selecting a plant exhibiting rapid root growth compared to a plant which was not introduced with the polynucleotide under obstacle-touching stress, wherein the plant exhibiting rapid root growth indicates that the plant has enhanced resistance to obstacle-touching stress.

12. The method according to claim 11, wherein the plant cell is selected from the group consisting of protoplasts, gamete producing cells and cells which regenerate into a whole plant.

13. The method of claim 11, wherein the plant cell is monocotyledon or dicotyledon.

* * * * *